(12) United States Patent
Nevo et al.

(10) Patent No.: US 12,245,886 B2
(45) Date of Patent: Mar. 11, 2025

(54) GUIDANCE SYSTEM FOR INTERVENTIONAL DEVICES WITH CURVED SHAPE

(71) Applicant: ROBIN MEDICAL INC., Baltimore, MD (US)

(72) Inventors: Erez Nevo, Netanya (IL); Amir Roth, Modiin-Maccabim-Reut (IL)

(73) Assignee: SCOPUS MEDICAL SYSTEMS, LTD., Nir Am (IL)

( * ) Notice: Subject to any disclaimer, the term of this patent is extended or adjusted under 35 U.S.C. 154(b) by 0 days.

(21) Appl. No.: 17/911,680

(22) PCT Filed: Mar. 16, 2021

(86) PCT No.: PCT/IB2021/052177
§ 371 (c)(1),
(2) Date: Sep. 15, 2022

(87) PCT Pub. No.: WO2021/186342
PCT Pub. Date: Sep. 23, 2021

(65) Prior Publication Data
US 2023/0134815 A1    May 4, 2023

Related U.S. Application Data

(60) Provisional application No. 62/989,926, filed on Mar. 16, 2020.

(51) Int. Cl.
| | |
|---|---|
| A61B 8/08 | (2006.01) |
| A61B 17/34 | (2006.01) |
| A61B 34/00 | (2016.01) |
| A61B 34/10 | (2016.01) |
| A61B 34/20 | (2016.01) |

(52) U.S. Cl.
CPC ............ *A61B 8/0841* (2013.01); *A61B 34/25* (2016.02); *A61B 2017/3413* (2013.01); *A61B 2034/107* (2016.02); *A61B 2034/2051* (2016.02)

(58) Field of Classification Search
None
See application file for complete search history.

(56) References Cited

U.S. PATENT DOCUMENTS

| | | | |
|---|---|---|---|
| 8,348,861 B2 * | 1/2013 | Glozman | A61B 34/20 600/407 |
| 2005/0159676 A1 * | 7/2005 | Taylor | A61B 10/0275 600/564 |
| 2012/0220894 A1 | 8/2012 | Melsheimer | |
| 2016/0361122 A1 | 12/2016 | Seeber | |
| 2019/0117187 A1 * | 4/2019 | Patel | A61B 8/4483 |
| 2021/0212728 A1 * | 7/2021 | Greening | A61B 17/43 |

FOREIGN PATENT DOCUMENTS

WO    2019/227151 A1    12/2019

* cited by examiner

*Primary Examiner* — Jonathan Cwern
(74) *Attorney, Agent, or Firm* — AlphaPatent Associates Ltd.; Daniel J. Swirsky

(57) ABSTRACT

A system and method for guidance of a device having a curved needle to a target tissue includes a tracking system having an imaging component, a processor, and a curved needle with known geometric parameters. The processor is configured to calculate a needle trajectory based on geometric considerations of the needle and the target tissue. Additional features and methods of the invention include a display with an annotated overlay for directing and tracking the curved device.

18 Claims, 17 Drawing Sheets

GUIDANCE SYSTEM FOR INTERVENTIONAL DEVICES WITH CURVED SHAPE

CROSS-REFERENCE TO RELATED APPLICATIONS

The present application is a national stage application of PCT/IB2021/052177 filed on Mar. 16, 2021, and which claims the benefit of US Provisional Patent Application No. 62/989,926, filed Mar. 16, 2020.

FIELD

The invention relates to a system and method for guidance of a curved interventional device and more specifically a curved needle.

BACKGROUND

Tracking systems are widely used in medical practice to assist in the insertion of various devices (e.g., biopsy needles, ablation probes, catheters, endoscopes) into the target organ or location. The devices can be largely classified into rigid devices with a straight insertion path (e.g. biopsy and ablation devices) and flexible devices with insertion paths that can follow various trajectories (e.g. catheters and endoscopes). The former devices are typically inserted transcutaneously (i.e. through the skin and underneath tissues) to the target, sometimes with image guidance (e.g. ultrasound, X-ray, CT, MRI) and sometimes by manual palpation (e.g. in breast biopsy).

The current disclosure is intended for the transcutaneous insertion of devices under imaging guidance. Currently, most of the devices that are inserted this way are straight—biopsy needles, RF ablation probes, cryo-ablation probes. The device may slightly bend during the insertion, and this may result in inaccurate placement of the device into the target. Some solutions to this problem are being developed, for example the use of fiberoptic sensors to measure the needle bending (Patent application 20150190123). Another approach is to provide a steerable front end of the device, as used in many surgical tools for laparoscopic procedures (e.g. LaproFlex, Deam, The Netherlands). A few rigid devices use a curved needle that is initially inserted towards the target in a straightened configuration within a needle guide, and then deployed into the target while returning to its curved shape (e.g. Pakter curved needle (Cook Medical, USA); Avaflex for vertebroplasty (Stryker, USA); Star bone tumor ablation device (Merit Medical, USA); U.S. Pat. Nos. 6,592,559; 7,713,273; 10,123,809).

PCT patent application publication number WO2020100038A3, incorporated by reference herein in its entirety, discloses the use of curved needles with fixed geometry for biopsies.

However, guidance of curved needles using a tracking system such as is used for a straight device remains a challenge. There is thus a need for a guidance system and method that enables planning of the insertion position of a device with a curved component such as a curved biopsy needle, and for guidance of the device into the target.

SUMMARY

The following specification describes a guidance system for a guidance of a curved device to a target in a body and methods of use thereof. The system and method may include tracking and imaging for calculation and optimization of reaching the target.

There is provided, in accordance with embodiments of the invention, a system for guidance of a curved needle to a target tissue in a body. The system includes a curved needle having a curved section, the curved section configured to curve in a flexion plane and having known curvature parameters. The curved needle is enclosed within a straight needle guide, such that when enclosed within the straight needle guide, the curved section of the curved needle is straight, and upon distal deployment of the curved needle from the straight needle guide, the curved section that is deployed from the straight needle guide is curved with the known curvature parameters within the flexion plane. The system further includes a tracking system configured for tracking a position of the curved needle and the straight needle guide in the body, wherein the tracking system further includes an imaging component. The system further includes a processor configured to calculate a needle trajectory, the needle trajectory including a needle guide insertion length and a needle deployment length such that the curved needle is configured to reach the target tissue when said needle guide insertion length and said needle deployment length are used. The calculating is done based on the known curvature parameters, a chosen entry point, and a location of the target tissue. The system further includes a graphic user interface for displaying the calculated needle trajectory. In some embodiments, the known curvature parameters includes a known radius of curvature wherein the radius of curvature is constant.

In accordance with further features in embodiments of the invention, the system may include a sensor positioned on the curved needle or on the device. In accordance with further features in embodiments of the invention, the tracking system may be a tracking system with a three-dimensional scanning capability and is configured to track the position of the curved needle based on data from the sensor. The imaging component is configured to provide a scanning plane which includes the target tissue and an intersection line of the flexion plane with the scanning plane so that a rotated position of the curved needle may be determined for the chosen entry point such that when in the determined rotated position, the flexion plane of the curved needle includes the target tissue, thus providing the curved needle with capability of reaching the target tissue when deployed from the straight needle guide.

In accordance with further features in additional embodiments of the invention, the tracking system may be capable of providing two dimensional images, and the imaging component includes a probe with a two-dimensional scanning plane. The curved needle may be attached to the probe of the imaging component such that the flexion plane of the curved needle is in alignment with the two-dimensional scanning plane.

In accordance with further features in additional embodiments of the invention, the chosen entry point is offset from the target tissue. In some embodiments, the curved needle is a curved biopsy needle.

In accordance with further features in additional embodiments of the invention, the graphic user interface may display an image from the imaging component and may further display annotations on the image for guiding the device based on the calculated needle trajectory.

In accordance with further features in additional embodiments of the invention, the system may further include an automated controller, wherein the processor provides the calculated needle trajectory to the automated controller and the automated controller is configured to advance the curved needle to the target based on the calculated needle trajectory.

There is provided, in accordance with embodiments of the invention, a method for guidance of a curved needle to a target tissue. The method includes providing a curved needle having a curved section, the curved section configured to curve in a flexion plane and having known curvature parameters, the curved needle enclosed within a straight needle guide, such that upon distal deployment of the curved needle from the straight needle guide, the curved section that is deployed from the straight needle guide is curved with the known curvature parameters within the flexion plane, providing an imaging component for providing images of the target tissue and of the curved needle with respect to the target tissue, choosing an entry point into a body for the curved needle enclosed within the straight needle guide, positioning the straight needle guide with the curved needle therein at the entry point, calculating a needle guide insertion length, advancing the straight needle guide with the curved needle therein into the body by the calculated needle guide insertion length, calculating a needle deployment length, and advancing the curved needle distally past a distal end of the straight needle guide by the calculated needle deployment length until the target tissue is accessed.

In accordance with further features in embodiments of the invention, the method may include rotating the straight needle guide with the curved needle therein to align a flexion plane of the curved needle such that the target tissue can be accessed upon deployment of the curved needle or maintaining a position of the straight needle guide and rotating the curved needle within the straight needle guide to align a flexion plane of the curved needle such that the target tissue can be accessed upon deployment of the curved needle. The method may further include accessing a second target tissue by calculating a second needle guide insertion length and a second needle deployment length, retracting the curved needle back into the needle guide, repositioning the needle guide at the second needle guide insertion length, and advancing the curved needle distally past a distal end of the straight needle guide by the second needle deployment length.

In accordance with further features in embodiments of the invention, the method may include taking a tissue sample once the target tissue is accessed. The method may further include calculating a needle trajectory based on the calculated needle guide insertion length and on the calculated needle deployment length. Calculating the needle trajectory may be done by providing a starting orientation vector from a distal end of the straight needle guide to a point which is transversely adjacent the target tissue, providing a target vector from a distal end of the straight needle guide to the target tissue, calculating an angle between the orientation vector and the target vector, and based on the known curvature parameters calculating the projected needle trajectory.

In accordance with further features in embodiments of the invention, the method may include displaying the target tissue and the calculated needle trajectory.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further aspects of the invention may be better understood by referring to the following description in conjunction with the accompanying drawings in which.

Figure 1:
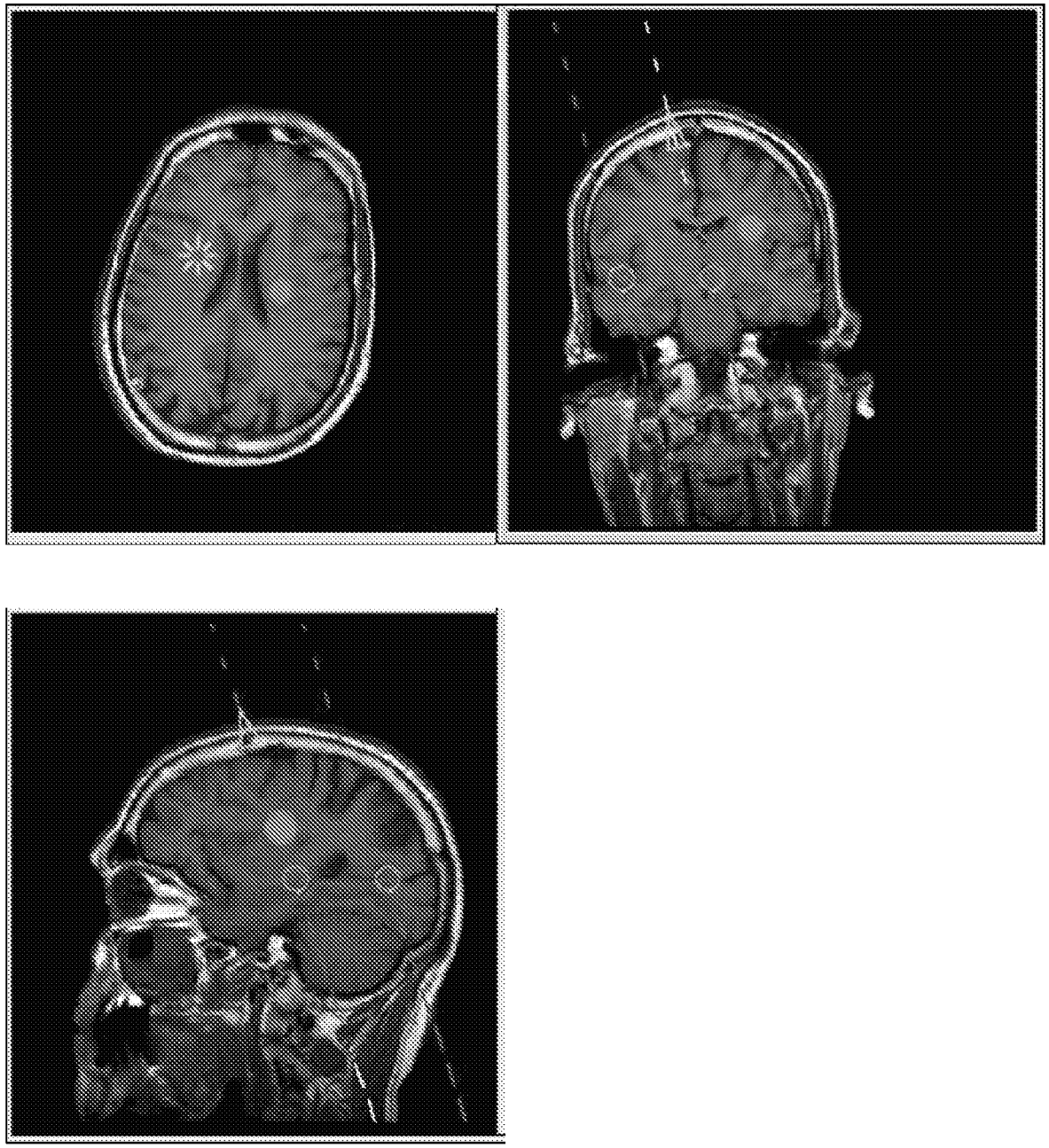
FIG. 1 is a photographic illustration of three orthogonal images with tracking annotation superimposed thereon for a straight needle configuration.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the invention. It will be understood by those of ordinary skill in the art that the invention may be practiced without these specific details. In other instances, well-known methods, procedures, components and structures may not have been described in detail so as not to obscure the invention.

Embodiments of the invention are directed to systems and methods for guiding a device within a body, and more particularly to guiding a curved device within a body. The systems and methods of the invention are designed to provide guidance for an interventional device having a curved shape to enable samples to be obtained from one or multiple locations within a target, which can later be used for both microscopic histopathology analysis and biomarker analysis of the tissue properties in these different locations. Alternatively, the interventional device can be configured for other uses, examples of which include but are not limited to treatment of multiple locations by heat deposition, or by injection of therapeutic agents, or by freezing. The principles and operation of systems and methods according to the invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Although the description herein is directed specifically to a biopsy device including a biopsy needle, it should be readily apparent that other curved devices may be guided using similar systems and methods and fall within the scope of the invention.

Guidance of a device with a straight needle can be done by tracking the position (location and orientation) of the device and superimposing a display of the needle tip location and needle orientation on scans that are acquired by imaging systems such as, but not limited to, X-ray, ultrasound, CT or MRI. An example of this type of guidance system is the EndoScout™ tracking system for MRI (disclosed in U.S. Pat. Nos. 6,516,213 and 9,037,213, incorporated by reference herein in their entireties). The graphic user interface (GUI) of the EndoScout™ adds tracking annotation to images from MRI scanners to help a user guide the device. An example of images from such a system is shown in FIG. 1, which is an illustration showing the use of three orthogonal images with tracking annotation superimposed thereon. The images shown in FIG. 1 are for a straight needle configuration. For this type of needle, two or three views are shown (three in the example shown in FIG. 1), which enables alignment of the device to the target. In the case of a straight device, even a single view that shows the target and the needle position (location and orientation) in reference to the scan plane can suffice to enable guidance of the needle to the target. However, when a curved needle is used, guidance is more complex. The invention, in embodiments thereof, is directed to guidance of a device with a curved needle.

Figure 2:
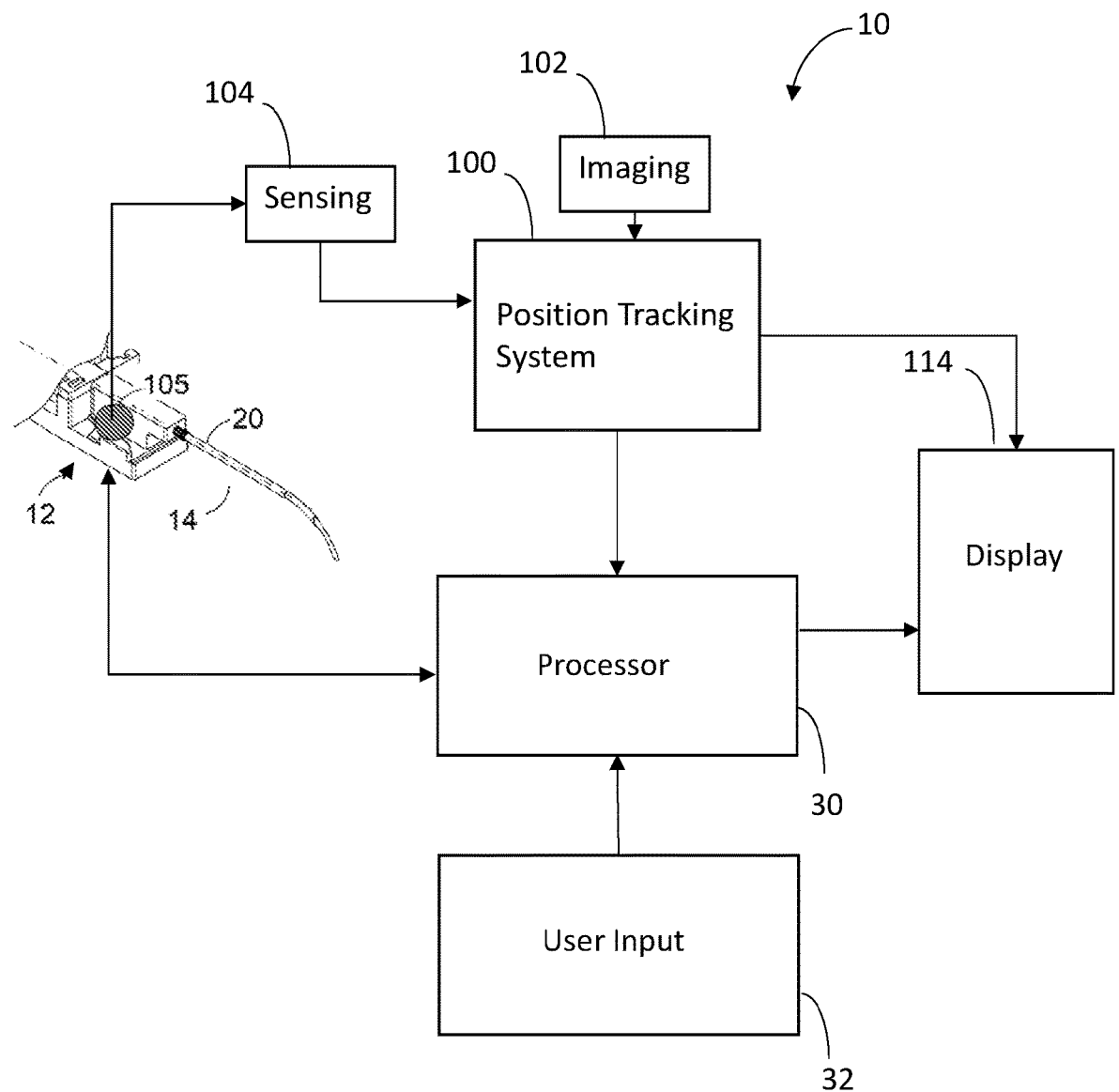
FIG. 2 is schematic illustration of a guidance system for guidance of a device having a curved needle, in accordance with embodiments of the invention.

Reference is now made to FIG. 2, which is a schematic illustration of a guidance system 10 for guidance of a device 12 having a curved needle 14, in accordance with embodiments of the invention. System 10 includes a device 12 having a needle with a curved configuration, wherein in the present embodiment device 12 is a core biopsy device with a curved needle 14 positioned within a needle guide 20. Examples of a curved needle 14 and a needle guide 20 for positioning of the curved needle 14 therein are described in PCT publication WO2020100038A3, incorporated herein by reference in its entirety. It should be readily apparent that the description herein with respect to a curved needle and a core biopsy device should be taken as illustrative, and that other curved interventional devices are included within the scope of the invention.

Figure 3A:
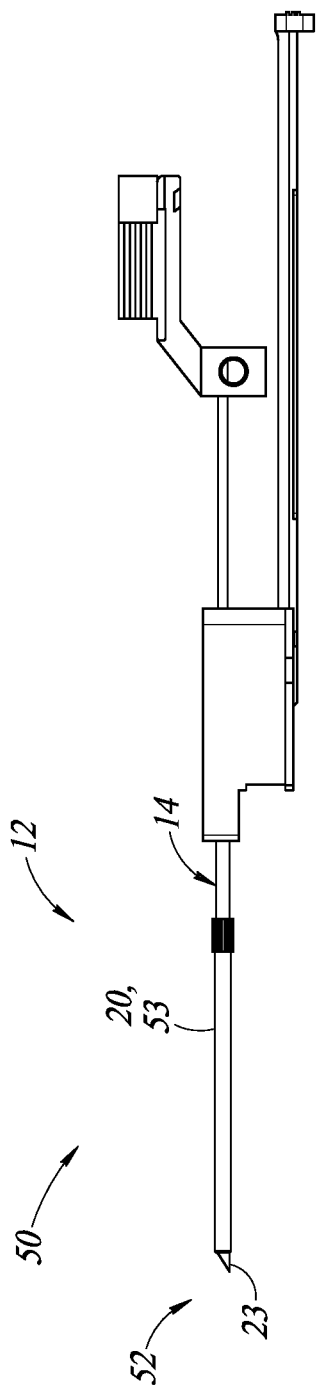
FIGS. 3A and 3B are illustrative examples of a device having a curved needle positioned within a needle guide, wherein the device is a core biopsy device, and the curved needle is a core biopsy needle positioned within a straight coaxial needle guide, in accordance with embodiments of the invention.
Figure 3B:
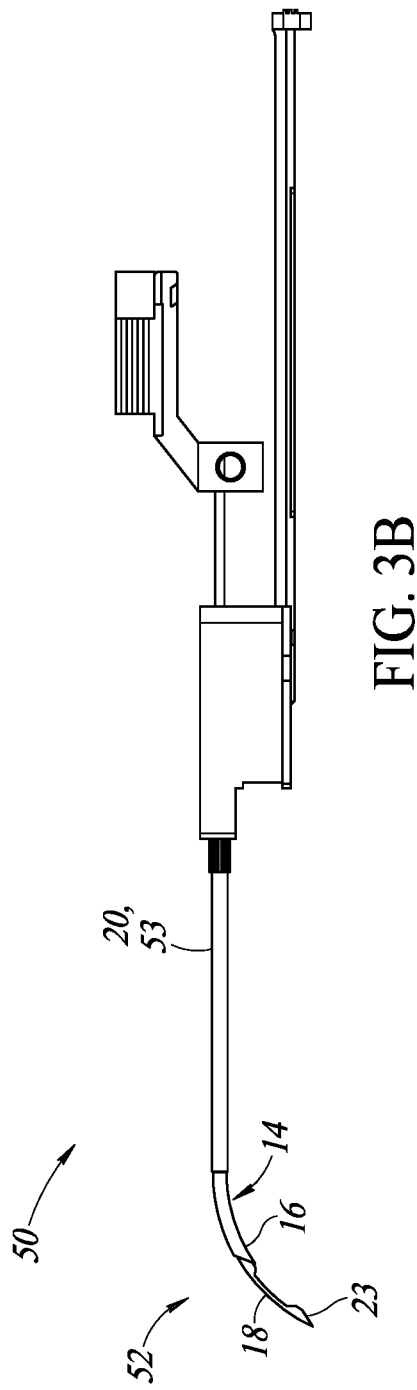

Reference is now made to FIGS. 3A and 3B, which are illustrative examples of a device 12 having a curved needle 14 positioned within a needle guide 20, wherein device 12 is a core biopsy device 50, and curved needle 14 is a core biopsy needle 52 positioned within a straight coaxial needle guide 20 (in this case, a core biopsy straight coaxial needle guide 53). Core biopsy needle 52 includes a stylet 18 and a cutting cannula 16. As shown in FIG. 3A, when core biopsy needle 52 is fully contained within coaxial needle guide 53, core biopsy needle 52 has a straight configuration. In this straight configuration depicted in FIG. 3A, core biopsy needle 52 can be inserted into the body and directed to the target, moved distally and proximally (i.e. forward and backward), and rotated either together with coaxial needle guide 53 or rotated with respect to coaxial needle guide 53 (with the needle guide not rotated). In the embodiment shown in FIG. 3A, coaxial needle guide 53 can be inserted into the body towards the target using image guidance, as is commonly done in current clinical practice of image-guided intervention. Once coaxial needle guide 53 is in place in the body, core biopsy needle 52 is advanced through coaxial needle guide 53 until core biopsy needle 52 is in the desired position. In some embodiments, coaxial needle guide 53 is attached to the core biopsy needle device via a connector, such as a Luer lock, for example. In either case, the ability to rotate core biopsy needle 52—either together with coaxial needle guide 53 or with respect thereto—is a key feature that enables the tip of the needle to reach different locations in a volume of interest.

Core biopsy needle 52 has a pre-curved configuration which is straightened when within coaxial needle guide 53.

As shown in FIG. 3B, when core biopsy needle 52 is deployed distally out of the needle guide 53, a tip 23 of core biopsy needle 52 bends back to its unloaded curved configuration, and as it is further deployed distally out of coaxial needle guide 53, tip 23 moves farther away from the center of coaxial needle guide 53. It should be readily apparent that device 12 of the invention is not limited to core biopsy device 50 depicted in FIGS. 3A and 3B, and that any device for insertion into a body which may assume a curved configuration is within the scope of the invention. Examples of other curved devices include, but are not limited to, heat ablation probes (where heat is generated by radiofrequency, microwave or laser); cryoablation probes (where tissue death is achieved by freezing); injection probes that can be used to inject drugs or lethal agents (e.g. ethanol injection) or to inject carrier agents (e.g. genetic material carriers like viruses, mRNA).

Figure 4A:
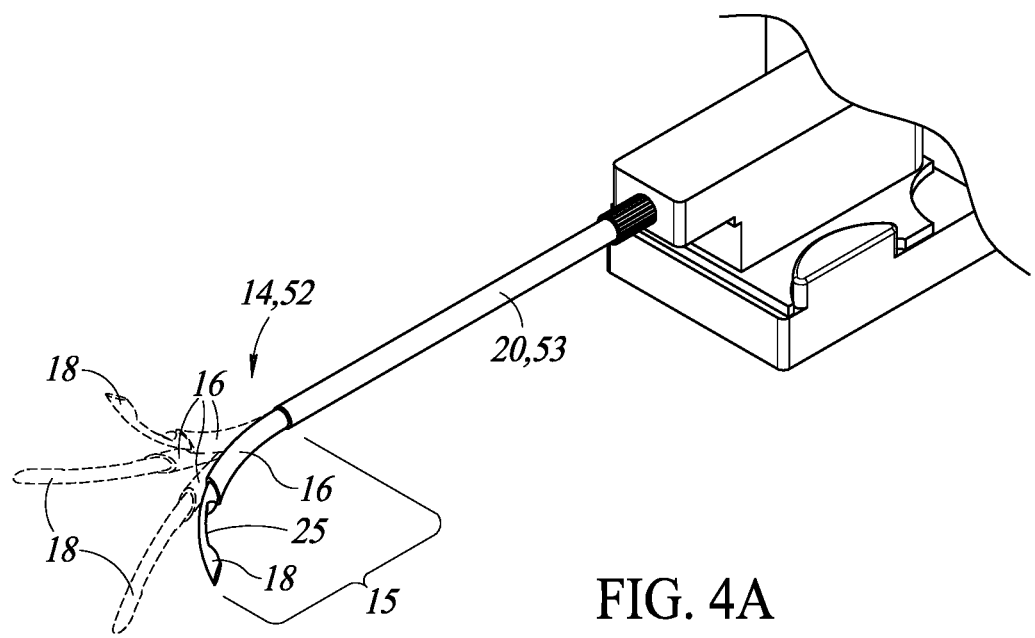
FIGS. 4A-4D are illustrations of the curved core biopsy needle of FIGS. 3A and 3B, showing the different tip positions that can be obtained through the combined use of rotation and forward motion (FIGS. 4A-4B), or through the use of needles with different radius of curvature (4C), taken together with the curved configurations of the curved core biopsy needle, and further showing a cylindrical volume around a needle guide for a needle having a given radius R1, R2 . . . Rn (FIG. 4D), in accordance with embodiments of the invention.
Figure 4B:
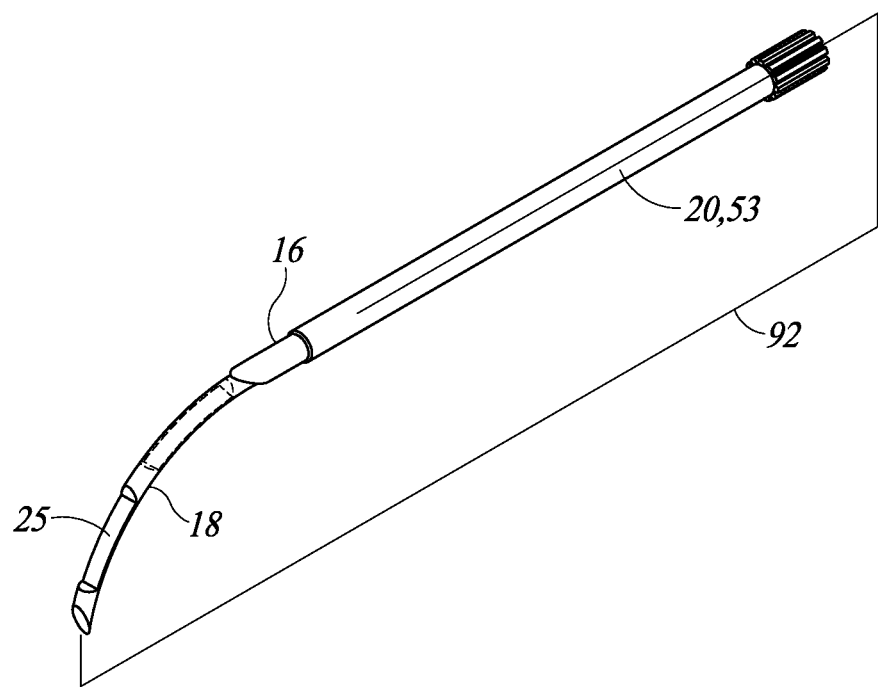
Figure 4C:
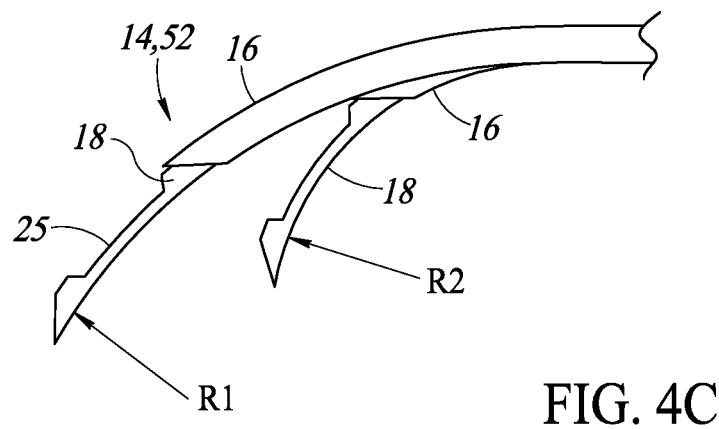

Reference is now made to FIGS. 4A-4D, which are illustrations of curved core biopsy needle 14, 52, showing the different orientations that can be obtained through the combined use of rotation and forward motion, taken together with the curved configurations of curved core biopsy needle 14, 52. As shown in FIG. 4A, when curved core biopsy needle 14, 52 including both a distal end of stylet 18 and a distal end of cutting cannula 16 are deployed out of coaxial needle guide 20, 53 and positioned distal to coaxial needle guide 20, 53, core biopsy needle 14, 52 assumes a curved configuration, and rotation of core biopsy needle 14, 52 (before being deployed from coaxial needle guide 20, 53) provides access to multiple locations at a range of 360 degrees. Curved core biopsy needle 14, 52 is shown in multiple positions rotationally in FIG. 4A. Curved core biopsy needle 14, 52 is in some embodiments only curved at a curved section 15 of curved core biopsy needle 14, 52. Rotation may be accomplished by rotating core biopsy needle 52 with respect to coaxial needle guide 20, 53. Alternatively, an entire device 12 such as core biopsy needle device 50 may be rotated from outside of the body; in this embodiment coaxial needle guide 20 and curved needle 14 are rotated together. As shown in FIG. 4B, stylet 18 may be deployed distally out of coaxial needle guide 20, 53 by different amounts, leading to different locations away from coaxial needle guide 20, 53. Stylet 18 is shown in FIG. 4B in two different positions as a schematic depiction of the many different possible distally deployed positions of core biopsy needle 52 with respect to coaxial needle guide 20, 53. It should be readily apparent that in embodiments of the invention, a distal end of cutting cannula 16 accompanies stylet 18 in its forward deployment. By combining the rotation of core biopsy needle 14, 52 within the needle guide 20, 53 (as shown in FIG. 4A), different positions (i.e. depth within the tissue) of coaxial needle guide 20, 53, and different amount of deployment of core biopsy needle 14, 52 from coaxial needle guide 20, 53 (as shown in FIG. 4B), the tip of the stylet 18 (shown with a notch 25, where the tissue sample is acquired) can be directed to any position around coaxial needle guide 20, 53, and a tissue sample can be acquired at many different locations within the target (e.g. tumor). This feature of combined rotation, translation and distal needle deployment provides complete coverage of tissue volume around core biopsy needle 14, 52. Also shown in FIG. 4B, a flexion plane 92 is defined as the plane within which curved needle 14 is configured to assume its curved shape. As shown in FIG. 4C, curved needle 14 may have various curvature parameters including, for example, various radii (R1, R2, . . . Rn), wherein the curvature parameters are important features in calculation of guidance parameters for guidance of device 12 to a target location. As shown in FIG. 4C, a core biopsy needle 14, 52 having a first radius of curvature R1 will advance farther away radially from coaxial needle guide 20, 53 than a core biopsy needle 14, 52 having a second radius of curvature R2 which is smaller than the first radius of curvature R1. Thus, the needle radius of curvature is a key geometric parameter used in calculation of guidance of device 12, as will be explained further hereinbelow. Needles of varying radii of curvature allows for penetration through different paths to the target.

It should be noted that such variations in design can be used to enable biopsy sampling "around a corner" in cases where direct line of penetration to the target cannot be achieved due to anatomic constraints. In some embodiments of the invention, the radius of curvature of curved needle 14 (R1 or R2 or any Rn) is constant. That is, the shape of curved needle 14 is a circular arc. This minimizes damage to the surrounding tissue.

Figure 4D:
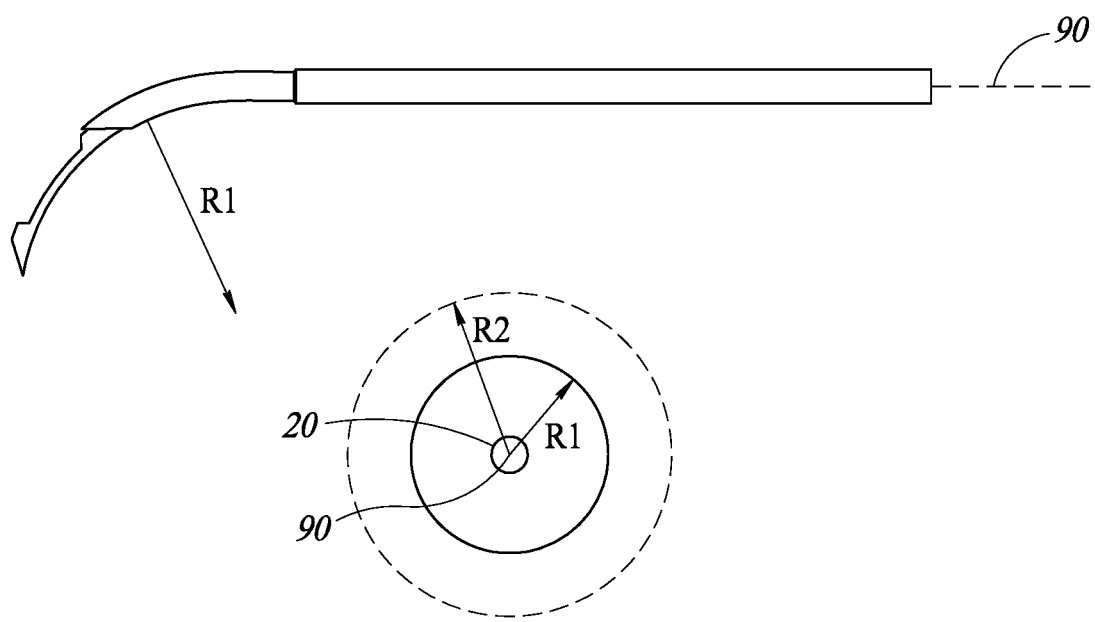

Reference is now made to FIG. 4D, which is a schematic illustration showing a cylindrical volume around needle guide 20 for a needle having a given radius R1, R2 . . . Rn. As shown schematically in FIG. 4D, an unlimited number of locations for obtaining tissue samples in a cylindrical volume around a longitudinal axis 90 of the needle guide 20 is available using a curved device as in the invention. The radius of such cylindrical volume equals the radius of the curved needle (R1 or R2 or any Rn). While this feature provides a significant advantage over straight devices, position and advancement guidelines for such a device is complex.

Returning now to FIG. 2, guidance system 10 further includes a position tracking system 100, a processor 30 and a display 114.

Position Tracking System 100

In embodiments of the invention, position tracking system 100 is provided to allow a user to accurately direct curved needle 14 to targets in radial positions away from a needle insertion path and to register tissue acquisition sites on images of the targeted organ. Position tracking system 100 includes an imaging component 102 for imaging of the body tissue, and a sensing component 104 for sensing a position of curved needle 14 within the body tissue.

Imaging component 102 may be, for example, MRI, CT, ultrasound, or any other suitable imaging system. A system for tracking a device 12 such as a biopsy device using MRI gradient fields is the EndoScout™ Tracking System (Robin Medical Inc., Baltimore, MD). The EndoScout™ Tracking System uses gradient fields of an MRI scanner to determine positioning of a device such as a biopsy needle in reference to MR images. In some embodiments that are based on non-MRI imaging (e.g. ultrasound, CT, X-ray), a tracking system such as the Aurora electromagnetic tracking system by Northern Digital Inc. (Waterloo, Ontario, Canada) can be used similarly to the use of the EndoScout™ in MRI-guided interventions.

In one embodiment, tracking system 100 has three-dimensional scanning capability, and imaging component 102 is configured to display either orthogonal images of the three-dimensional scan, or a three-dimensional display of the three-dimensional scan. In another embodiment, tracking system 100 has a two-dimensional scanning capability, and imaging component 102 has a probe with a two-dimensional scanning plane.

In the embodiment wherein the three-dimensional scanning capability is used, sensing component 104 may include one or more tracking sensors 105 attached to curved needle 14. Tracking sensor 105 provides the position and orientation of curved needle 14. Tracking sensor 105 can be positioned in various locations. In some embodiments, tracking sensor 105 may be positioned inside a body of the device 12, as depicted in FIG. 2. The body of device 12 may include an enclosure that has within it a proximal end of needle 14 and a deployment mechanism, for example. In additional embodiments, tracking sensor 105 may be positioned around a proximal end of the coaxial needle guide 20, 53 or around a proximal end of the needle 14. In yet additional embodiments, tracking sensor 105 may be positioned at the tip 23 of needle 14 (for example, at a tip of stylet 18 and/or cannula 16). In the following description, tracking sensor 105 is positioned inside the body of device 12, but it should be readily apparent that similar results should be obtainable when tracking sensor 105 is placed at another location. Data from imaging component 102 and sensing component 104 are integrated by position tracking system 100. These data may be sent to processor 30 for use in further calculations as will be described hereinbelow.

Figure 13A:
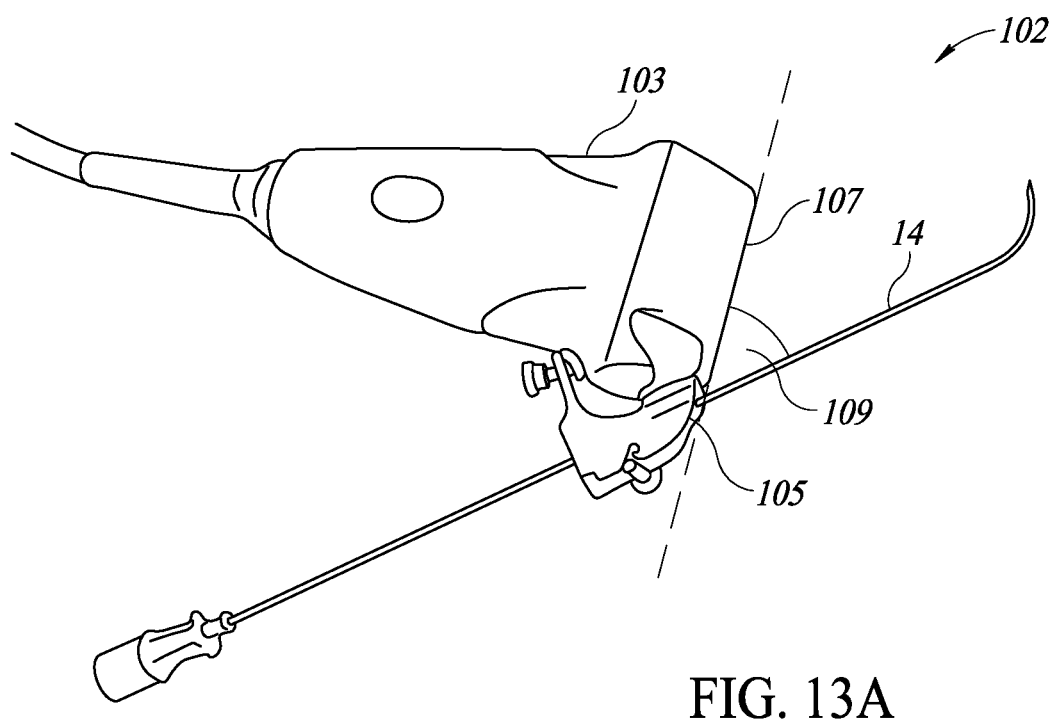
FIGS. 13A and 13B are illustrations of an imaging component having a probe with a scanning element depicting a needle attached to the probe in an angled orientation and in an aligned orientation, respectively, in accordance with embodiments of the invention.
Figure 13B:
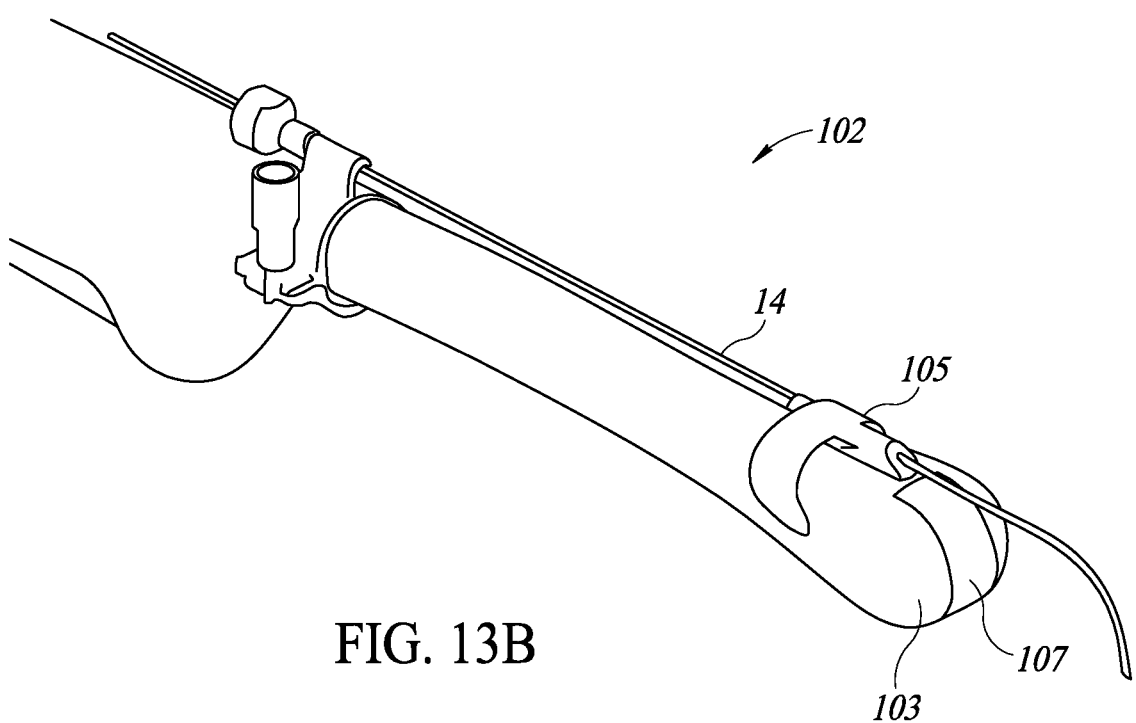

In the embodiment wherein two-dimensional scanning capability is used, a sensor may not be necessary. Reference is now made to FIGS. 13A and 13B, which are illustrations of imaging component 102 having a probe 103 with a scanning element 107 for providing a two-dimensional scanning plane. In the embodiment shown herein, imaging component 102 is an ultrasound imaging system, and probe 103 is an ultrasound probe. Needle 14 may be attached to probe 103, for example, using a probe connector 105. A scanning plane of imaging component 102 is determined by the position of scanning element 107. In one embodiment, as shown in FIG. 13A, needle 14 is oriented at an angle 109 to scanning element 107 and thus is at an angle 109 to a center line of the two-dimensional scanning plane produced by scanning element 107. In another embodiment, as shown in FIG. 13B, needle 14 is aligned along a scanning plane of imaging component 102 as produced by scanning element 107. Since the needle 14 is oriented with respect to probe 103 at a known angle 109, the flexion plane with respect to imaging component 102 is known. This known parameter can be used in the calculations for guidance, as will be described further hereinbelow.

Processor 30 is configured to collect tracking data from position tracking system 100 and to further collect user data from a user input 32, which may be collected before and/or during operation of guidance system 10. Processor 30 is configured to process the collected data and to provide output to display 114 so that the user can use the processed data for guidance. In some embodiments, an automated system may include a configuration wherein processor 30 is configured to provide output directly to an automated controller for curved needle 14 so that a position of curved needle 14 can automatically be adjusted based on data from processor 30.

Figure 5:
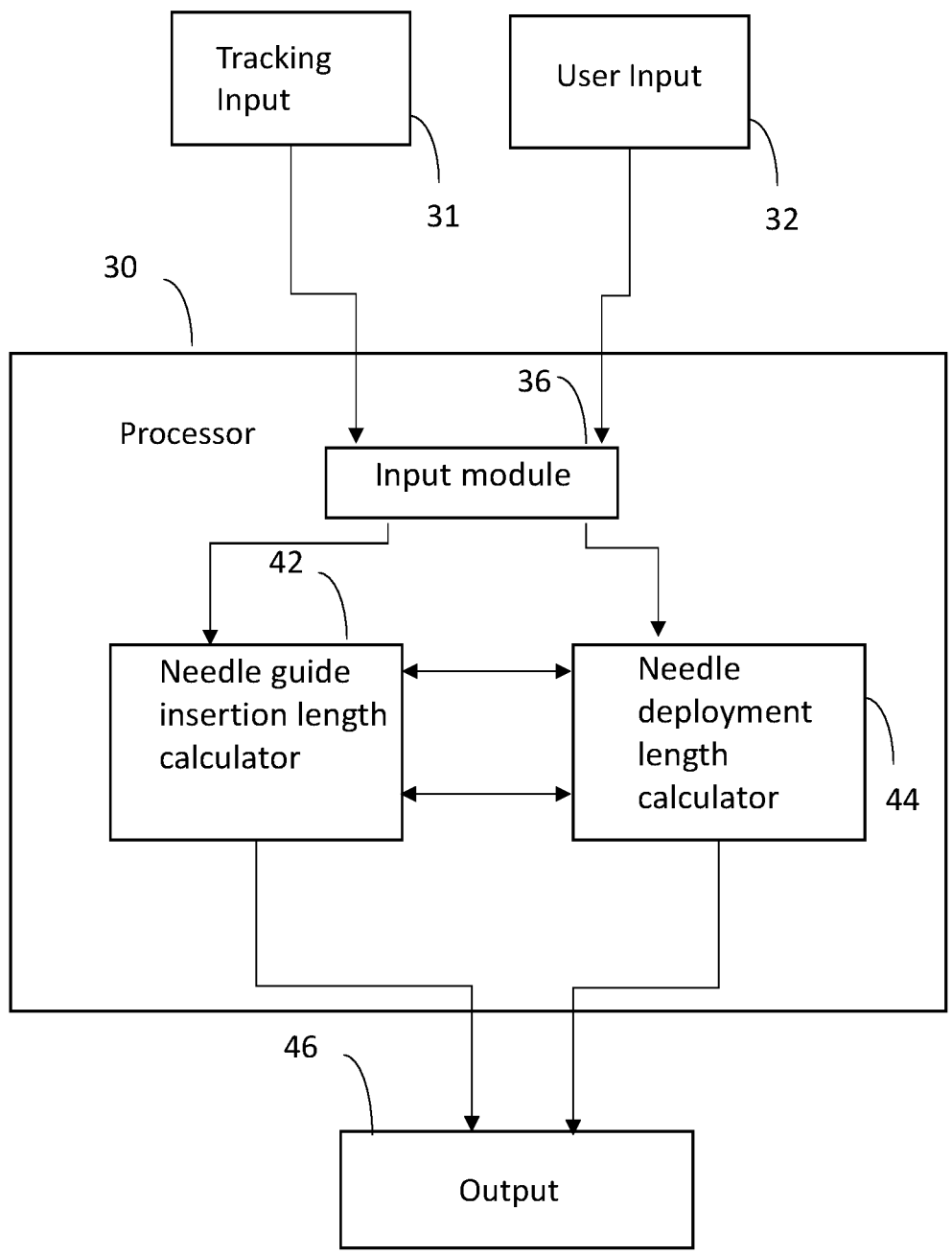
FIG. 5 is a schematic illustration of a processor of the guidance system of FIG. 2, showing various components of the processor in accordance with embodiments of the invention.

Reference is now made to FIG. 5, which is a schematic illustration of processor 30 showing various components of processor 30 in accordance with embodiments of the invention. Processor 30 includes an input module 36 which is configured to receive user input 32 and tracking input 31 from position tracking system 100. User input 32 may be received by input module 36 via a keyboard, mouse, or other input means. Tracking input 31 may be received by input module 36 via wired or wireless electronic communication between tracking system 100 and input module 36 of processor 30. Processor 30 further includes a coaxial needle guide insertion length calculator 42, a needle deployment length calculator 44 and an output 46.

Figure 6A:
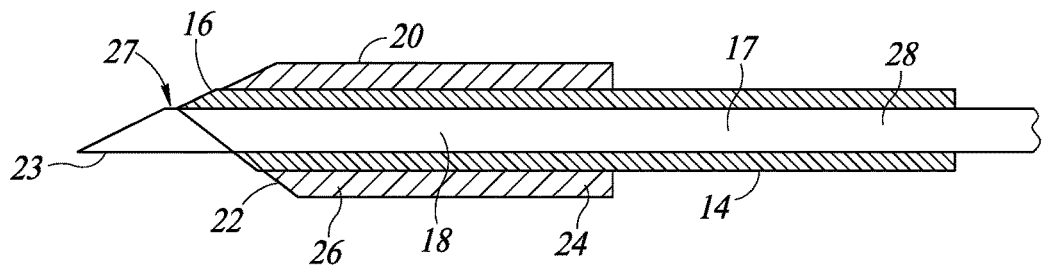
FIGS. 6A-6D are cross-sectional and schematic illustrations of the curved needle and needle guide, and their positions with respect to a body tissue.

Reference is now made to FIGS. 6A-6D, which are schematic illustrations of curved needle 14 and needle guide 20, and their various positions within a body. FIG. 6A is a cross-sectional illustration of curved needle 14 fully enclosed within needle guide 20. Needle guide 20 has a needle guide distal end 22 configured to enter the body tissue, a needle guide proximal end 24, which is accessible to a user (e.g. by attachment to a body of the biopsy device) and can be manipulated in a translational and rotational direction, and a needle guide body 26 extending from needle guide proximal end 24 to needle guide distal end 22. Curved needle 14 includes a needle distal end 27 having a needle tip 23 (which, in the embodiment shown herein, comprises both a tip of stylet 18 and a tip of cannula 16), a needle proximal end 28 (which, in the embodiment shown herein, comprises both a proximal end of stylet 18 and a proximal end of cannula 16) which is accessible to a user and can be manipulated in a translational and rotational direction, and a needle body 17 (which, in the embodiment shown herein, comprises both a body of stylet 18 and a body of cannula 16) extending from needle proximal end 28 to needle distal end 17. Needle 14 is shown having two components: stylet 18 and cutting cannula 16. For simplification and for purposes of calculation, the description of advancement of needle 14 from needle guide 20 refers to both stylet 18 and cutting cannula 16 advancing together. Although in some embodiments, stylet 18 and cutting cannula 16 are independently movable with respect to one another, this feature is not described since it does not relate to the navigation of the needle to the target. In some embodiments, for example when needle 14 is used for ablation or injection, needle 14 is a single unit. In either case, in the following description, needle 14 is considered to be one unit that moves independently of needle guide 20 during deployment and insertion of needle 14 until a target tissue is reached. Needle guide proximal end 24 and needle proximal end 28 which are manipulatable, may be manipulated manually or may be manipulated via an automated system.

Figure 6B:
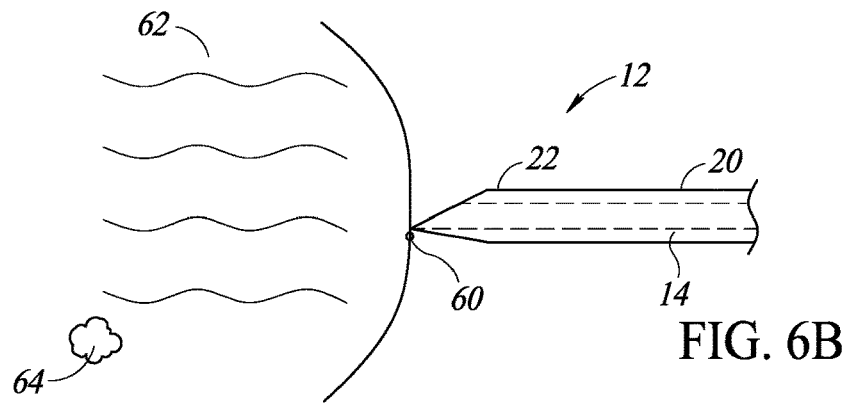
Figure 6C:
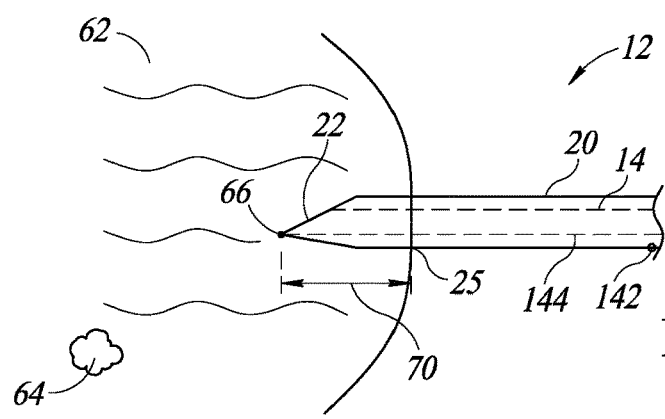
Figure 6D:
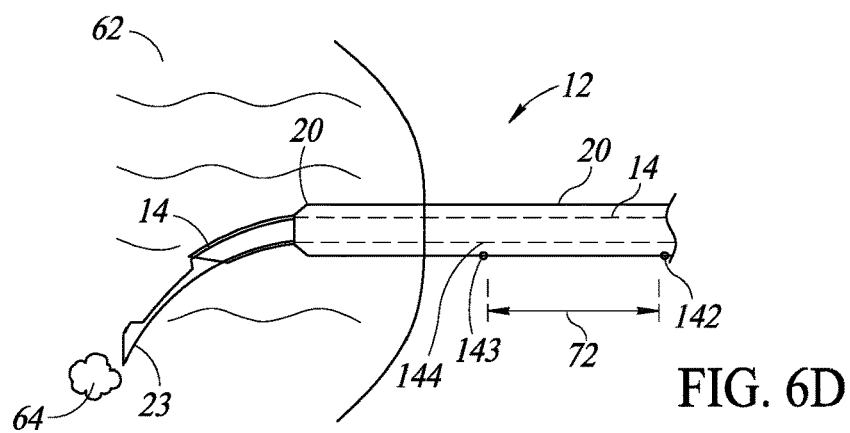

FIGS. 6B-6D are schematic depictions of device 12 including needle 14 and needle guide 20 at various positions with respect to a target tissue. In FIG. 6B, device 12 is shown positioned at an entry point 60 of a body tissue 62. Entry point 60 is a given parameter which may be decided by the user, for example, and which is a variable which can result in changes in calculations of other parameters as will be explained further hereinbelow. A target tissue 64 is shown at a location within a body tissue 62. Needle guide distal end 22 is shown exactly at entry point 60, prior to insertion of device 12 into body tissue 62. For a given entry point 60, the system 10 of the invention is configured to provide the following parameters to the user or to the automated system in order for the user to know how to manipulate device 12 so that curved needle 14 reaches target tissue location 64 in an accurate manner: a needle guide insertion length 70, a needle guide stopping point 66 within body tissue 62, and a needle deployment length 72. Needle guide deployment length 70 is defined as the length of needle guide which needs to be inserted into body tissue 62 such that needle guide distal end 22 is positioned at needle guide stopping point 66. This is shown schematically in FIG. 6C, wherein needle guide distal end 22 is at needle guide stopping point 66, thus defining an external needle guide position point 25. External needle guide position point 25 is the point along needle guide body 26 which is just external to entry point 60 of body tissue 62 when needle guide distal end 22 is at needle guide stopping point 66. Needle guide stopping point 66 is a location within body tissue 62 at which needle guide 20 stops being inserted into body tissue 62. Needle guide deployment length calculator 42 of processor 30 calculates needle guide deployment length 70 based on entry point 60 and needle guide stopping point 66.

Needle deployment length 72 is defined as the straight length of needle 14 which needs to be advanced from needle guide stopping point 66 such that needle tip 23 can reach target tissue 64. Since needle 14 is curved, needle deployment length 72 is not equal to the straight distance from needle guide stopping point 66 to target tissue 64, but rather is calculated based on curved needle radius R (R is a parameter which is intrinsic to needle 14. Different radii for needle 14 are designated by R1, R2 . . . Rn). However, for the purposes of the user, the straight length of curved needle 14 which corresponds to this distance is the parameter which must be used so that the user can know how far to push the needle until it reaches its target. Needle deployment length calculator 44 of processor 30 is configured to calculate needle deployment length 72. As shown in FIGS. 6C and 6D, in order to calculate needle deployment length 72, a needle starting position 142 on needle guide body 26 can be chosen. This needle starting position 142 is a point on needle guide body 26 which is aligned with a chosen point 143 of needle 14 prior to advancement of needle 14 with respect to needle guide 20. As shown in FIG. 6D, once needle 14 is advanced into the tissue, the chosen point 143 of needle 14 has advanced, and is now aligned with an ending position 144, which is the new point on needle guide body 26 associated with chosen point 143 of needle 14. The distance between starting position 142 and ending position 144 is defined as needle deployment length 72. Needle deployment length 72 thus represents the length of needle 14 which must be pushed proximally into the tissue once needle guide is held in place at needle stopping point in order for needle tip 23 to reach target tissue 64.

Figure 7:
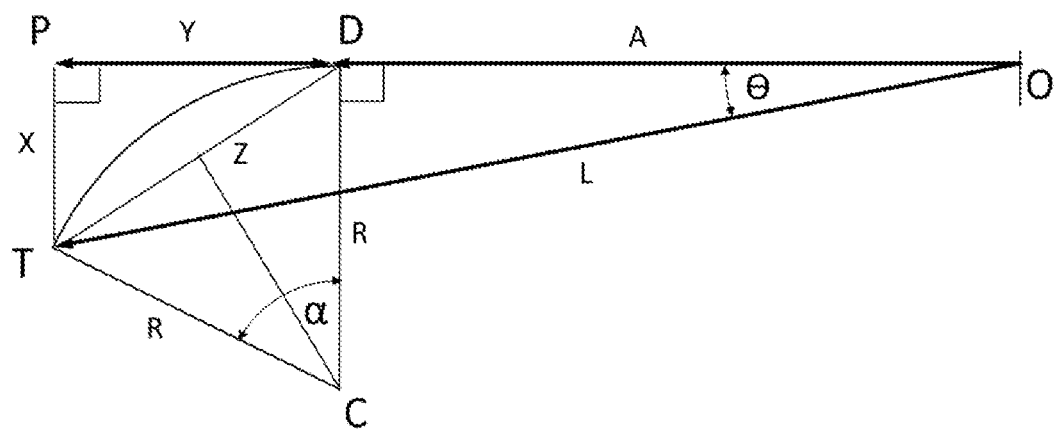
FIG. 7 is a geometric representation showing the parameters needed for calculating a needle guide deployment length and a needle deployment length in accordance with embodiments of the invention.

Reference is now made to FIG. 7, which is a geometric representation showing the parameters needed for calculating needle guide deployment length 70 and needle deployment length 72. For the purposes of calculation, device 12 including needle guide 20 and needle 14 is assumed to be oriented horizontally from point O to point P.

Point O is entry point 60;
Point D is needle guide stopping point 66;
Point T is the location of target tissue 64;
Point P is the cross point of a transverse line that connects the target point T and the needle orientation line; and
Point C is the center of curvature of a circular curved needle 14.
Vector OP is the starting orientation of the needle guide;
Vector OT is the direction from the needle tip to the target.
L is the distance from the tip of the needle guide to the target (segment OT);
A (segment OD) is the needle guide deployment length 70;
X (segment TP) is the transverse distance between target tissue location 64 and point P (i.e. the needle orientation line);
Z is the distance between points D and T;
Y is the distance between points P and D, which represents a straight line projection of needle deployment length 72 on the vector OP;
R is the radius of curvature of the curved needle (in this embodiment, the curved portion of the curved needle has a circular arc shape with constant radius of curvature R);
$\Theta$ is the angle between the OP and OT vectors; and
$\alpha$ is the angle of the curved needle arc.

The two key parameters that are calculated by processor 30 are A (needle guide deployment length 70) and $ARC_{TD}$ (curved needle deployment length 72). It should be readily apparent that these two parameters are related to one another and thus, if one changes, the other may change as well. Entry point 60 (point O) is a given, and when this value is changed, the other parameters will change accordingly.

Triangle OPT is a right-angle triangle, so X is given by the distance L and the angle $\Theta$:

$$X = L*\sin(\Theta) \tag{1}$$

and the distance of the segment OP (Y+A) is given by:

$$Y+A = L*\cos(\Theta) \rightarrow A = L*\cos(\eta) - Y \tag{2}$$

Triangle DCT is an isosceles triangle, so:

$$Z = 2R*\sin(\alpha/2) \tag{3}$$

The Sine Law in triangle TDO gives:

$$Z/\sin(\Theta) = L/\sin(180-\alpha/2) = L/\sin(\alpha/2) \tag{4}$$

Equations (3) and (4) can be combined to determine the angle $\alpha$:

$$2R*\sin(\alpha/2)/\sin(\Theta) = L/\sin(\alpha/2) \rightarrow \sin(\alpha/2) = \mathrm{SQRT}(L*\sin(\Theta)/2/R) \tag{5}$$

The Pythagorean theorem in triangle DTP gives Y from X and Z:

$$Y = \mathrm{SQRT}(Z^2 - X^2) \tag{6}$$

The different geometric variables are calculated as follows:
The distance L is calculated as the distance from point O (available from the tracking system) to point T (the target position determined by the user on the coordinate system of the tracking system).
The angle $\Theta$ is calculated as the angle between the vector OP (available from the tracking system) and the vector OT (the vector pointing from the point O to the target position).
The distance X is calculated from L and $\Theta$ by equation (1).
The angle $\alpha$ is determined from L, R and $\Theta$ by equation (5).
The distance Z is determined from R and $\alpha$ by equation (3).
The distance Y is calculated from Z and X by equation (6).
The distance A is calculated from Y, L and $\Theta$ by equation (2).

These parameters enable the advancement of the needle guide to point D (needle guide stopping point 66) where the deployment of the curved needle should be done. The length of deployment of the curved needle (needle deployment length 72) is determined by the length of the arc DT:

$$ARC_{TD} = R*\alpha \tag{7}$$

With the angle $\alpha$ in radians. Thus, as is clear from equation 7, needle deployment length 72 is dependent on radius R of curved needle 14.

Figure 8:
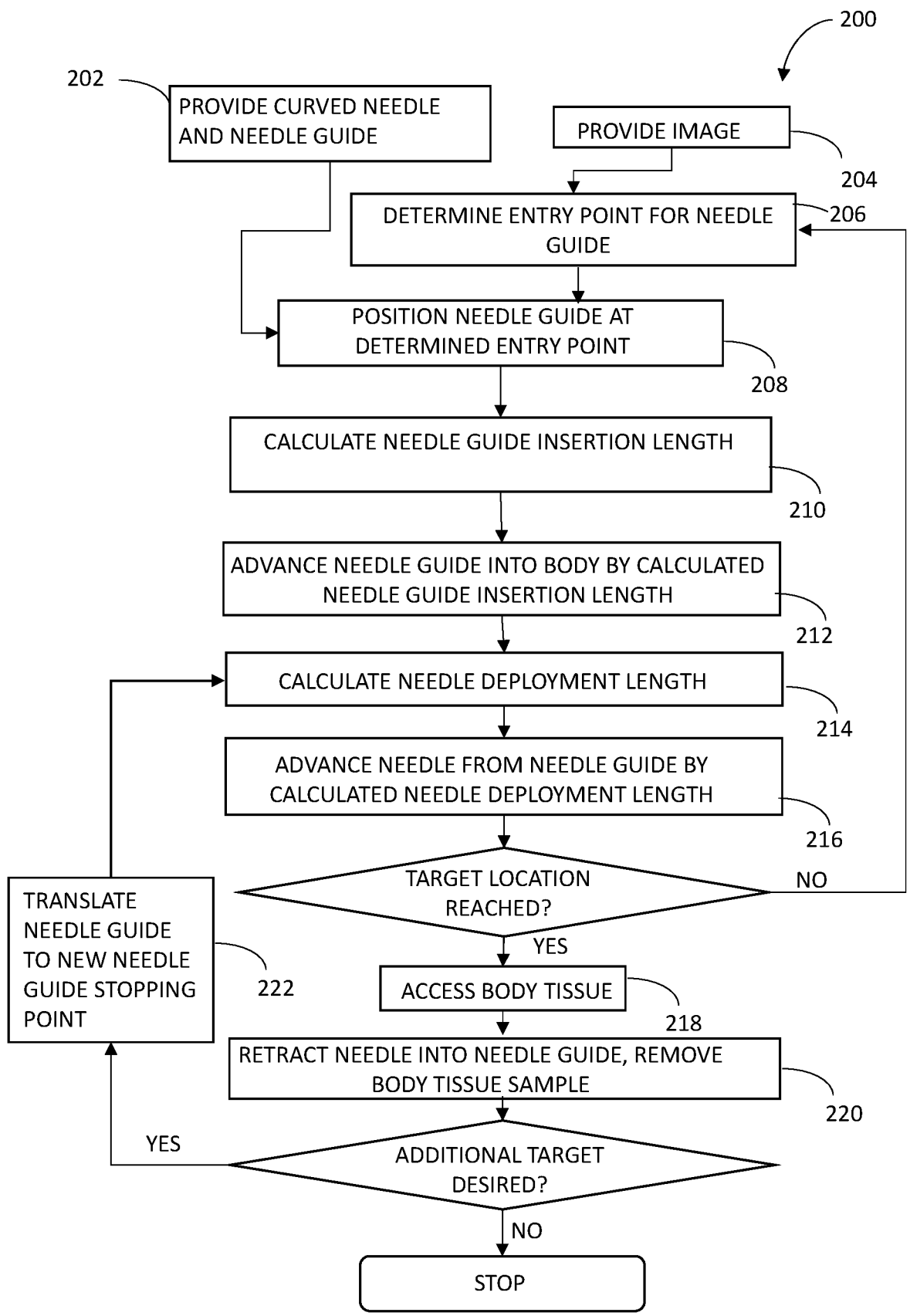
FIG. 8 is a flowchart illustration of a method of guidance of a curved needle to a target tissue, in accordance with embodiments of the invention.

Reference is now made to FIG. 8, which is a flowchart illustration of a method 200 of guidance of a curved needle to a target tissue, in accordance with embodiments of the invention. First, a curved needle within a straight needle guide is provided (step 202). Either before, after or simultaneously to providing the curved needle within the straight needle guide, imaging component 102 of position tracking system 100 provides (step 204) an image of a body tissue. The provided image may be a three-dimensional image, may be orthogonal views of a three-dimensional image, or may be a two-dimensional image. An entry point for the needle guide is determined (step 206) based on the provided image. The provided image includes the target or targets and critical anatomic structures that may obstruct access to a target (e.g. large blood vessel, nerves bundle, the gastrointestinal tract, bone). The user then positions (step 208) needle guide 20 with needle 14 positioned therein at the determined entry point 60. Positioning of the needle guide includes placement of the needle guide at the entry point 60, placing the needle guide 20 at a chosen orientation. Positioning of the needle guide may also include rotation of the needle guide 20 or keeping the needle guide steady while rotating the needle 14 within the needle guide 20. In some embodiments, needle 14 is not initially positioned within needle guide 20 and is only advanced therethrough once needle guide 20 is in its position in the tissue. In those instances, needle guide 20 may be inserted with an internal obturator that provides a sharp tip for the insertion of the needle guide 20 through the tissue). Processor 30 calculates (step 210) needle guide insertion length 70, and needle guide is advanced (step 212) into the body by the calculated needle guide insertion length 70 until needle guide stopping point 66. Processor 30 also calculates (step 214) a needle deployment length 72 and the needle is advanced (step 216) from the needle guide by the calculated needle deployment length 72. It should be readily apparent that the steps of calculating may be done before or interspersed with the steps of advancing, such that in some embodiments processor 30 does all of the calculating, after which device 12 is positioned and advanced, but in other embodiments, calculating is done during advancement, and may be based on imaging or sensing of device 12 during the procedure. If the target location has been reached, then the body tissue is accessed (step 218) and the relevant procedure (such as biopsy, for example) can be performed. If the target location has not been reached, then a new entry point may be determined, and new calculations may be made. In some embodiments, this process may be repeated until the target tissue is reached. Tracking system and/or imaging system continues to track the deployment of the curved needle and to calculate adjustments so that the curved needle reaches the target.

Optionally, for example when the procedure is biopsy, the curved needle 14 is retracted (step 220) back into the needle guide 20 and a tissue sample obtained in the procedure is unloaded for further analysis, as described in PCT patent publication WO2020100038A3.

In some embodiments, multiple target locations may be desired, and since needle 14 is curved, it is possible to access various locations without moving needle guide 20, or to reach various locations with re-positioning of needle guide 20. If an additional target location is desired, the curved needle 14 is retracted back into the needle guide 20, a new needle guide stopping point 66 may need to be calculated for the new target location and the needle guide 20 may need to be translated (i.e. moved forward or backward) to the new stopping point 66 (step 222). After needle 14 is retracted back into the needle guide 20, it may need to be rotated so the flexion plane of the curved needle is aligned such that the new target location is accessible. A new needle deployment length 72 is calculated (step 214) and needle 14 is advanced by the calculated new needle deployment length 72 to the new target.

Graphic User Interface

A particular feature of the invention, in embodiments thereof, is display 114, designed to present real-time position and orientation of curved needle 14 and needle guide 20 (as provided by position tracking system 100) overlaid on an image of target tissue 64.

Figure 9:
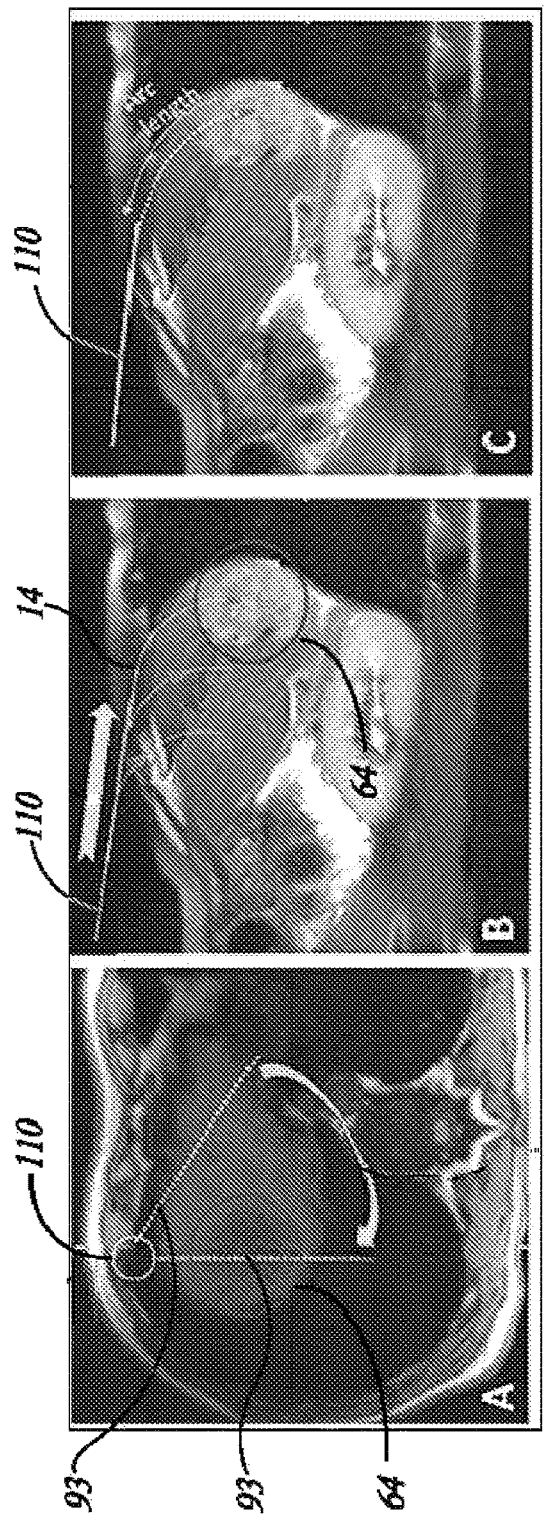
FIGS. 9A-9C are illustrations of a display showing annotations overlaid over images from the imaging component of the system of FIG. 2, when tracking system has a three-dimensional scanning capability, in accordance with embodiments of the invention.

Reference is now made to FIGS. 9A-9C, which are photographic illustrations of display 114 showing annotations 110, when using a tracking system 100 with a three-dimensional scanning capability. Annotations may include an overlay of calculated values with images from imaging component 102, and may further show a calculated needle trajectory, for example. FIG. 9A shows an image from the imaging component 102 of tracking system 100, having target tissue 64 therein, and annotation of the intersection line 93 between the flexion plane 92 of the needle and the image plane (which may be the scanning plane in 2D imaging, or generated from 3D imaging data). The flexion plane 92 may not include the target tissue initially, but as device 12 and/or needle 14 is rotated, the annotation of intersection line 93 is rotated over the image (white arrow) until it reaches the target tissue 64, which indicates that flexion plane 92 includes the target tissue therein, thus providing the curved needle 14 with capability of reaching the target tissue when deployed from the straight needle guide.

FIG. 9B shows different projected positions of needle 14 based on advancement of needle guide 20 to various locations (i.e. various needle guide stopping points). It is clear from FIG. 9B that one of the parameters which determines whether needle 14 will reach target tissue 64 is the needle guide insertion length 70. The needle guide is advanced (white arrow) until the projected curved needle trajectory reaches the target 64. FIG. 9C is an illustration of deployment of the curved needle 14 by calculated needle deployment length 72 (depicted in FIG. 9C as "Arc Length"), such that curved needle tip 23 reaches target tissue 64. It should be readily apparent that an arc length of needle 14 corresponds to needle deployment length 72 as calculated by processor 30 and described above with reference to FIGS. 6A-6D and FIG. 8.

Figure 10:
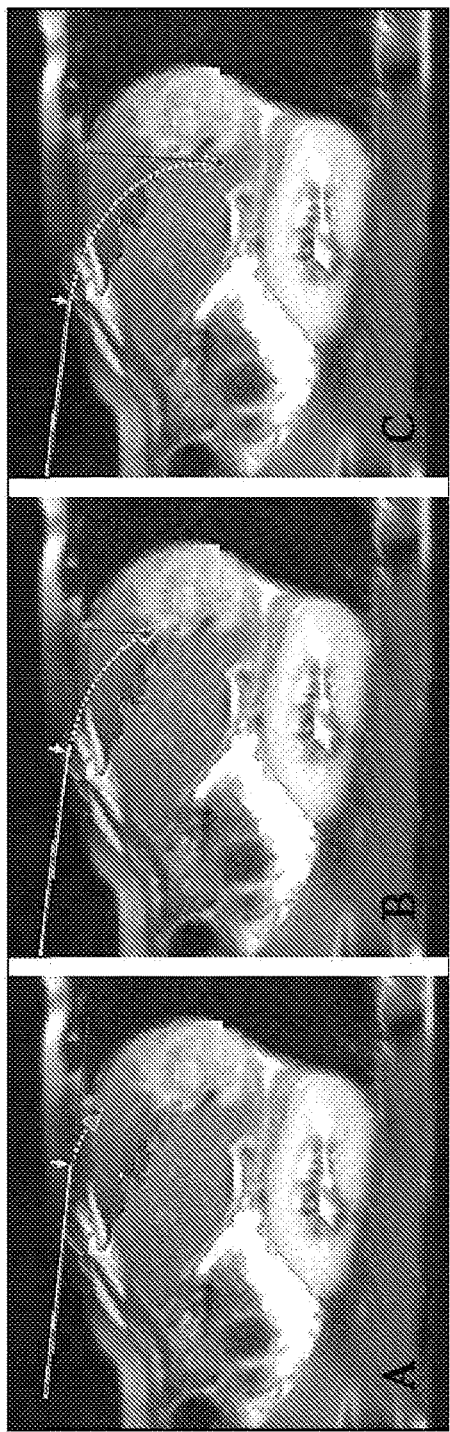
FIGS. 10A-10C are illustrations of a display as in FIGS. 9A-9C, showing three different target locations, wherein differences in needle guide deployment length and in needle deployment length both result in reaching different locations.

In some embodiments, multiple target locations are desired. Reference is now made to FIGS. 10A-10C, which are photographic illustrations showing three different target locations, wherein differences in needle guide insertion length 70 and in needle deployment length 72 both result in reaching different locations. As shown in FIG. 10A, a first needle guide insertion length and a first needle deployment length are used to reach a first location (arrow head). As shown in FIG. 10B, a second needle guide insertion length and a second needle deployment length are used to reach a second location (arrow head). As shown in FIG. 10C, the second needle guide insertion length is maintained (white arrow in FIGS. 10B-10C), but a third needle deployment length is used to reach a third location (arrow head). These two parameters may be varied in order to reach multiple locations. While changing these two parameters enable access to different targets in a single plane, rotation of the straightened curved needle within the straight needle guide (or rotation of the whole device, including the needle guide and the straightened curved needle in it) enables access to targets in different planes, and thus provides device 12 the possibility to reach any point in a cylindrical volume around the needle guide insertion line, as described with reference to FIG. 4D above. It is thus a feature of the invention, in embodiments thereof, that by using the various calculations, multiple target locations may be reached. This can be done manually or automatically based on processor 30.

Figure 14A:
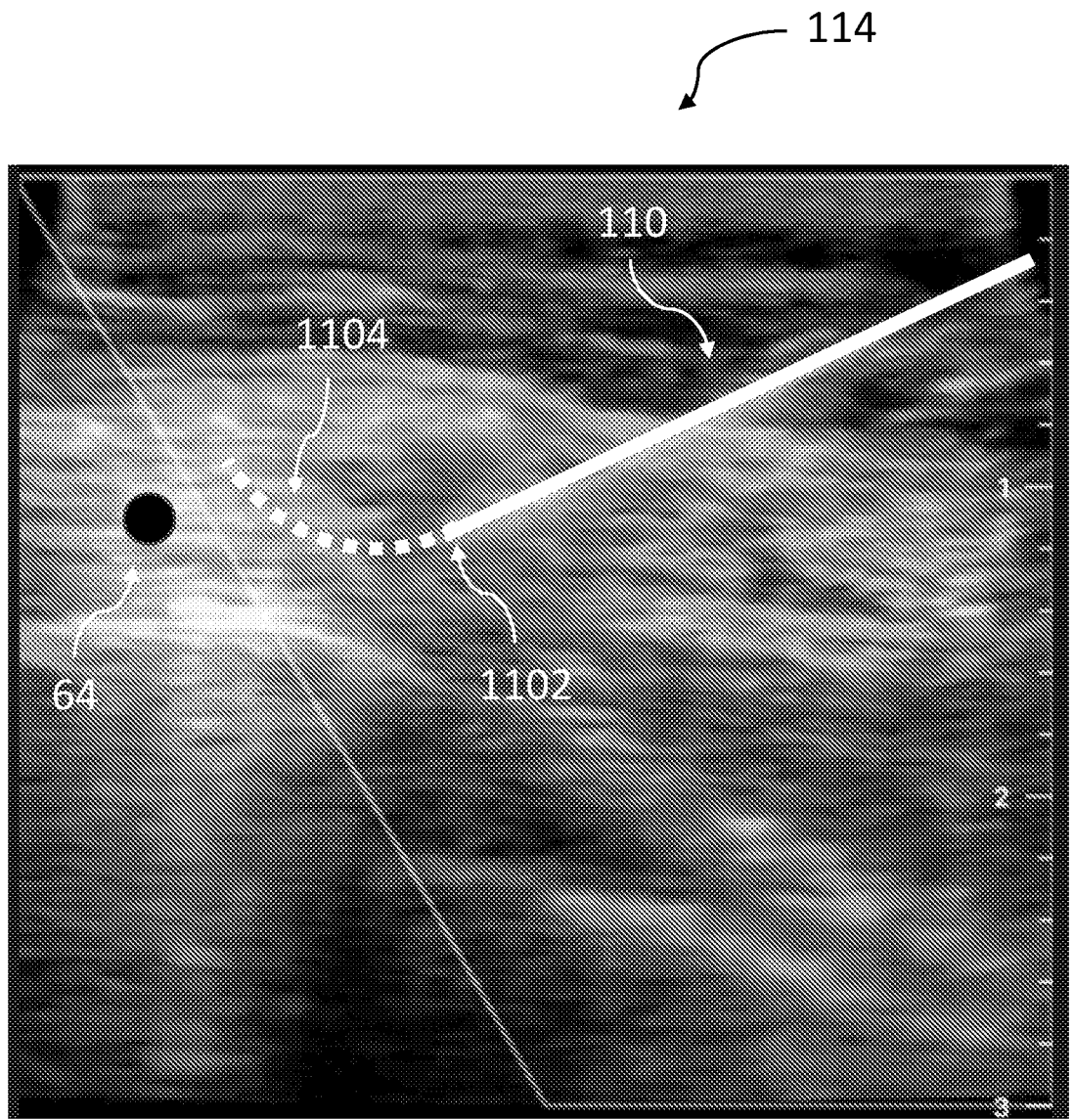
FIGS. 14A and 14B are photographic illustrations of a display showing annotations when using a tracking system with a two-dimensional scanning capability, in accordance with embodiments of the invention.
Figure 14B:
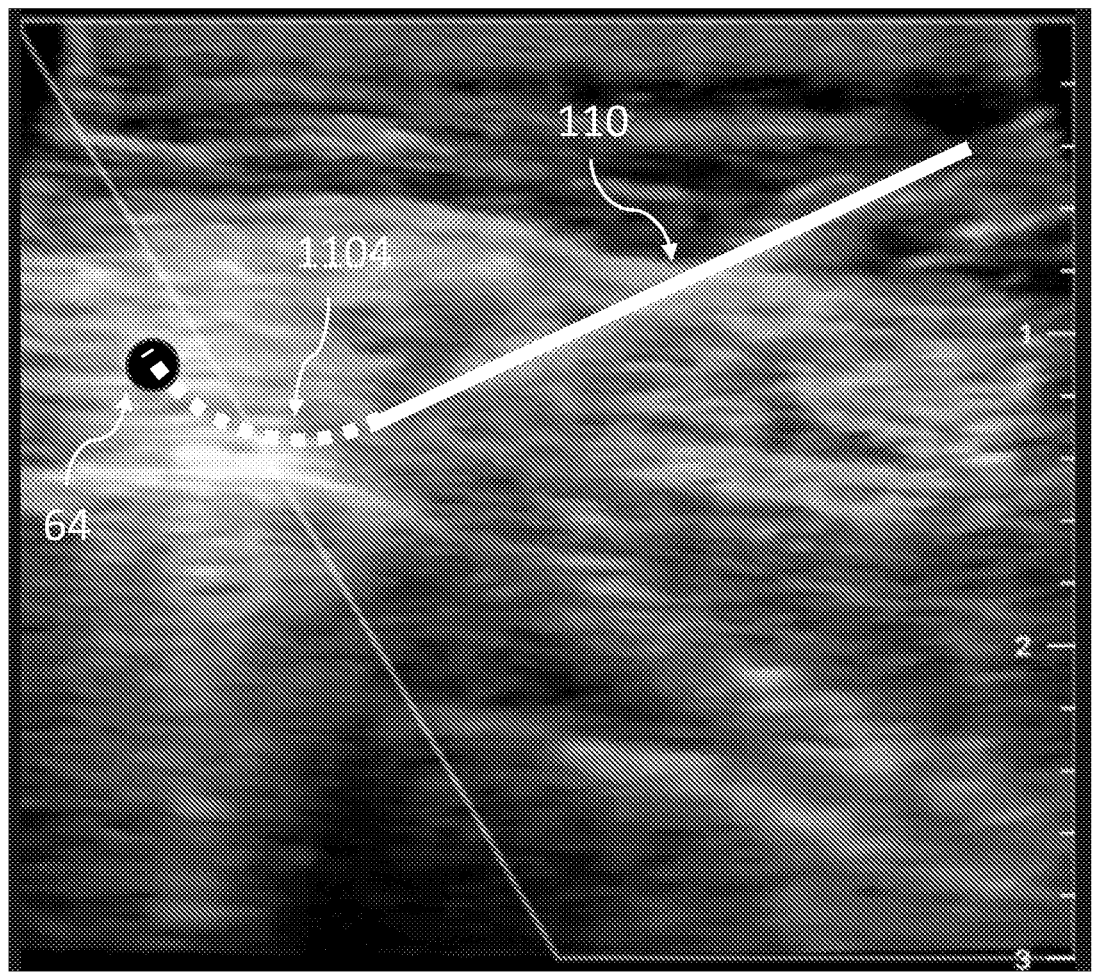

Reference is now made to FIGS. 14A and 14B, which are photographic illustrations of display 114 showing annotations 110, when using a tracking system 100 with a two-dimensional scanning capability. As described above with reference to FIGS. 13A and 13B, when imaging component 102 with a two-dimensional scanning capability is used, such as an ultrasound probe, needle 14 may be attached to the probe such that orientation of flexion plane 92 with respect to target tissue 64 is known. As an example, a clinical grade ultrasound scanner used to guide needle insertion can provide automatic detection of the needle artifact in the scan, and graphic annotation of the detected needle is added over the ultrasound real-time scan (for example Needle Viz™, Butterfly Networks, Inc., Guilford, CT, USA). Since the ultrasound scan is planar, if the device 12 and/or needle 14 is positioned in the scanning plane, the device artifact in the scan images represents the device location and orientation in reference to the ultrasound probe and in reference to the organs that are scanned and seen in the scan images. An example of a probe connector 105 is a needle holder such as standard ultrasound needle guides (for example, Civco https://www.civco.com/products/ultrasound-needle-guides/). Thus, if the curved needle is attached to the ultrasound probe through a needle holder, and the flexion plane of the curved needle is aligned with the scan plane of the scanner, then the curved needle can be guided based on the tracking of the needle artifact in the scan images.

As shown in FIG. 14A, the tip (distal end) 1102 of the graphic annotation of the needle guide artifact in the scan images represents the tip of the needle guide. An arc 1104 having a radius equal to the radius of the curved portion of the needle, and length equal to the length of the curved portion of the needle, is generated and attached to the tip of the graphic annotation of the needle guide, that is overlaid in the ultrasound scan images. This arc represents the trajectory of the curved needle portion if the needle guide is stopped at the current position and the curved needle is deployed out of the needle guide. When the target is identified in the scan images, that is an indication that the scanning plane cuts through the target, and thus the flexion plane is also aligned such that the curved needle can reach the target.

As shown in FIG. 14B, once it is clear that the target is in alignment, the user can advance the needle guide deeper. As in the previous embodiment, the needle guide 20 is advanced by the calculated needle guide insertion length 70. The graphic annotations 110 of the needle guide and the arc at its tip is overlaid on the scan images. If the user advances the needle guide by the calculated needle guide insertion length 70, then the arc 1104 in the graphic annotation should cross the target, as shown in FIG. 14B. This is the stopping point of the needle guide 20. Alternatively, the user can advance the needle guide with continuous scan and monitor the advancement of the tracking annotation until the arc 1104 of the annotation reaches the target. The user can now deploy the curved needle by needle deployment length 72, and can monitor its progress until it reaches the desired point in the target.

Experimental Example

An experimental example of guidance of a device 12 with a circular curve with a known radius R using the system and methods of the invention is provided. In the present example, device 12 was a Pakter curved needle (Cook Medical) that has a proximal straight portion and a distal curved portion that can be deformed into a straight configuration within a straight needle guide. A commercial electromagnetic tracking system 100 (Aurora, Northern Digital Inc., Waterloo, ON) with a tracking sensor 105 for real-time tracking of the position (location and orientation) of device 12 was used. This was a simplified setup to provide guidance in a two-dimensional (2D) plane, similar to the embodiment wherein device 12 is attached to probe 103.

A guidance algorithm for the curved needle was programmed in Matlab. In the present example, the real-time position data of the needle was obtained from the tracking system 100. The target position was input by the user. The algorithm calculated the geometry of the system and presented a real-time guidance display enabling the operator to guide the curved device 12 to the target. In the experiment, the operator was able to input into the system different entry points and different needle guide orientations.

Figure 11:
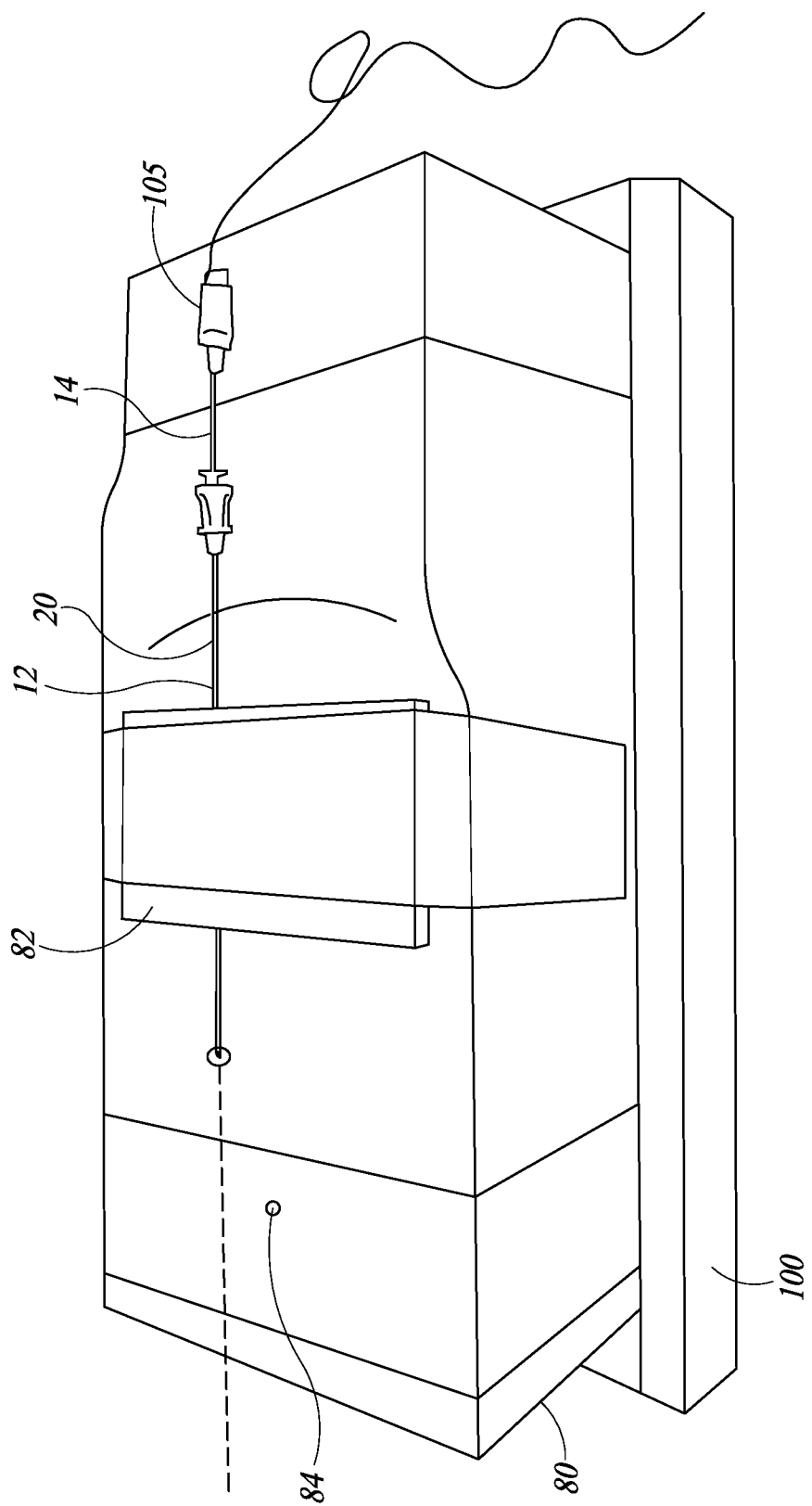
FIG. 11 is a schematic illustration of an experimental setup for testing calculation of parameters used in a guidance system for curved devices in accordance with embodiments of the invention.

Reference is now made to FIG. 11, which shows the experimental setup. As shown in FIG. 11, a thick foam 80 of approximately 10 cm in height was placed on the tracking field generator 100, simulating a body lying over the generator. A thin foam 82 of approximately 5 mm thickness was placed over thick foam 80. Thin foam 82 functioned as a device holder, in order to simulate a user operating device 12 or to simulate probe connector 105. Device 12 was placed on top of thick foam 80 and under thin foam 82 to simulate device 12 being held by the operator or by probe connector 105, and inserted into the body. The Aurora tracking sensor 105 was attached to the proximal end of the curved needle and provided the position of the needle tip and orientation of the needle guide (taking into account the distance between the sensor position at the proximal end of the needle and the needle tip). The sensor 105 was attached to the needle such that its axial direction was parallel to the direction of the straight part of the needle direction, and one of the transverse directions coincides with the direction of the curved needle flexion when it is deployed out of the needle guide (these two directions define the flexion plane of the curved needle that is used as the 2D guidance plane in this simplified experimental setup).

Figure 12A:
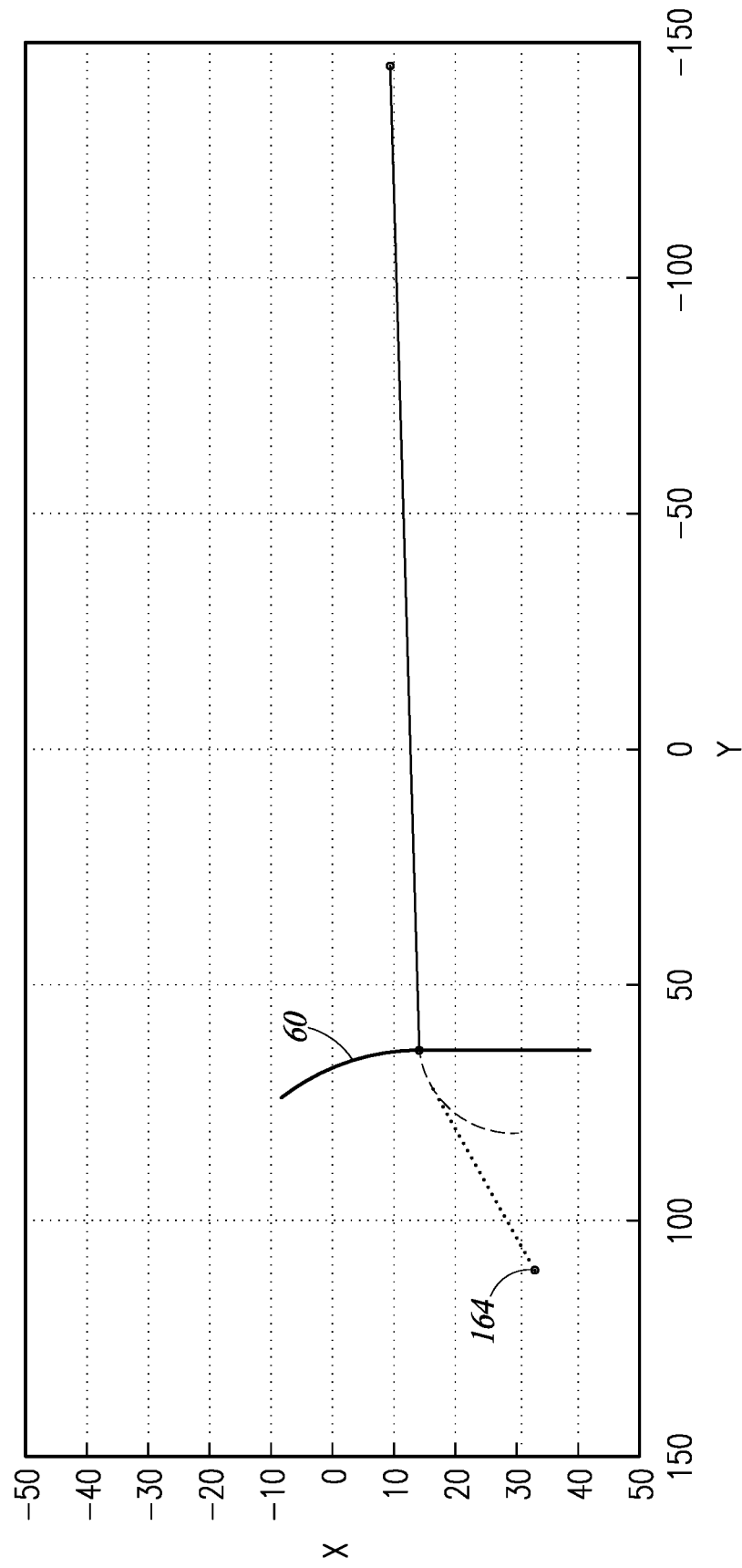
FIGS. 12A-12C are graphical illustrations showing a process of calculating values for guidance of a curved needle to a target location, in accordance with embodiments of the invention.
Figure 12B:
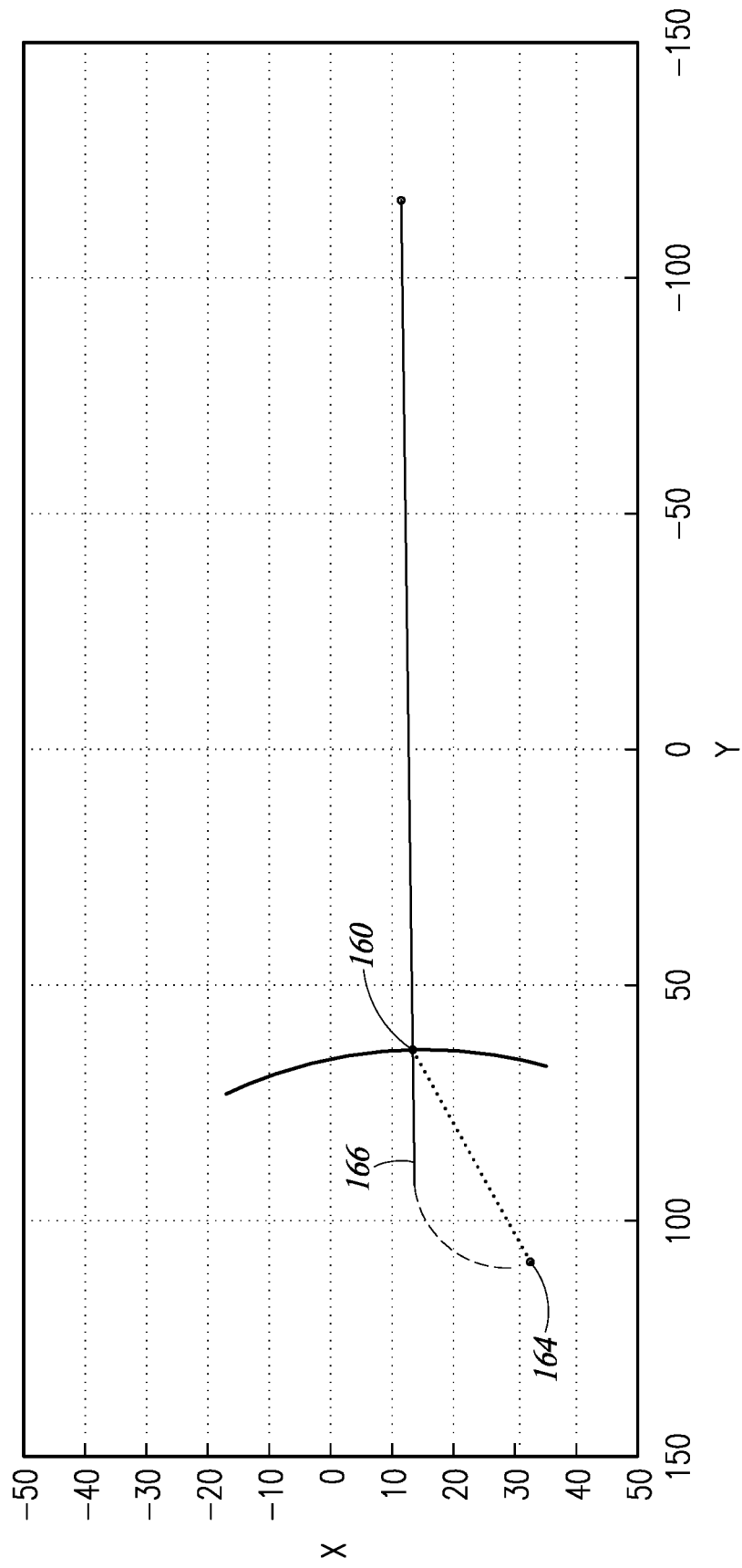
Figure 12C:
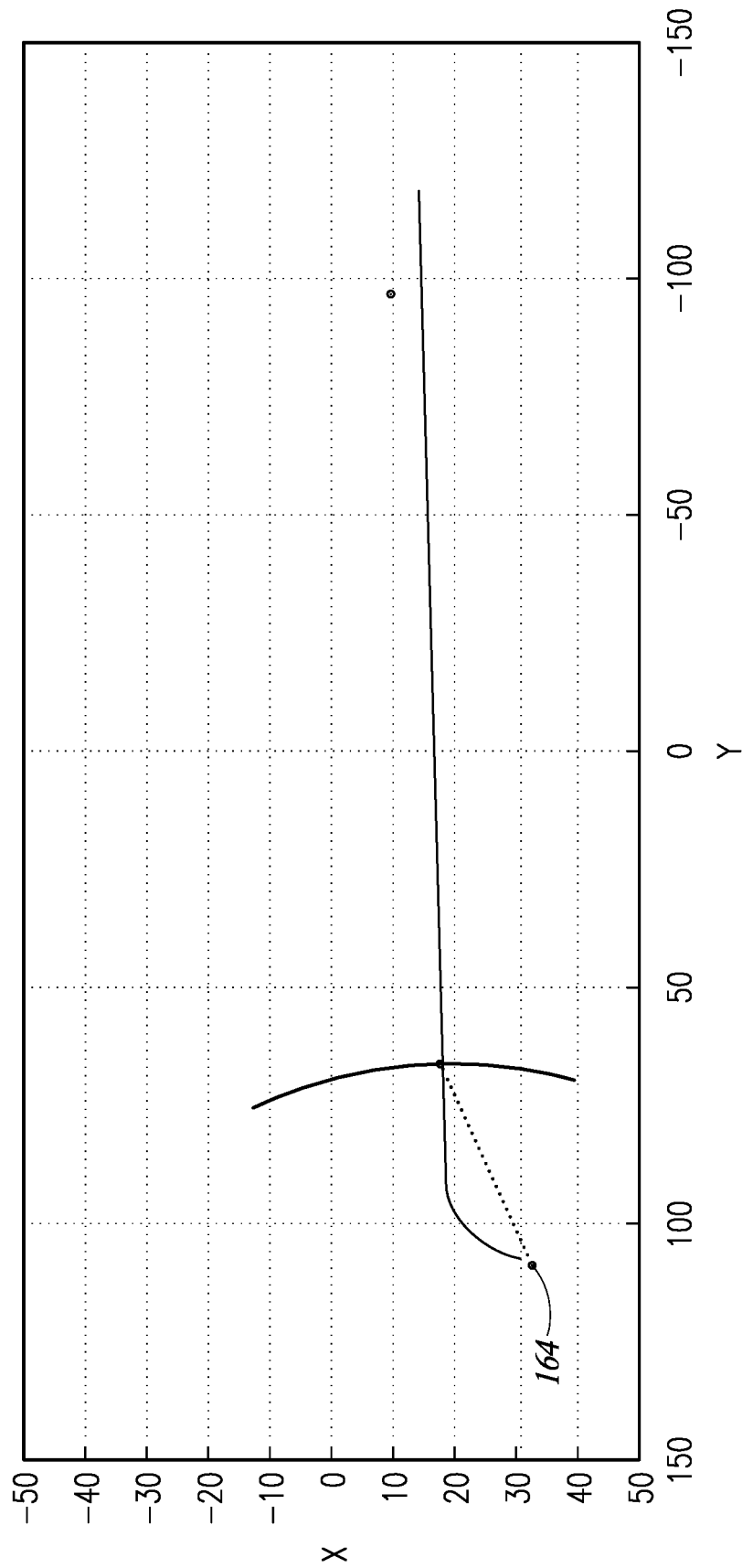

As shown in FIGS. 12A-12C, a laptop computer provides real-time 2D display of the needle position (location and orientation) that is registered to the flexion plane of the needle. A target position 84 was marked on thick foam 80 and target position 84 was tracked via a second tracking sensor that was temporarily placed over the position of the marked target (not shown).

During the planning phase (before insertion of needle guide 20 into the body) the operator chooses the entry point 60 to the body and rotates the needle to bring the flexion plane of the needle to include the target.

FIG. 12A depicts a screen view showing determination of the entry point 60 as follows: the needle guide encloses the curved needle in a straight configuration; the tip of the needle guide is placed at the entry point 60; the system verifies that a target 164 can be reached by the tip of the curved needle and displays a line to the target. At this point the operator presses a "set" button to set the entry point 60.

FIG. 12B depicts a screen view showing needle guide insertion: The operator pushes forward the needle guide to reach needle guide stopping point 166. At needle guide stopping point 166, the curved trajectory line (shown as a dashed line) reaches the target 164. At this point the needle guide should not be moved further and the curved needle should be deployed and advanced to the target. Now the operator pushes the "Start Curve" button and moves to the deployment phase.

FIG. 12C depicts a screen view showing needle deployment. Once the "Start Curve" button is pressed, the system assumes that the curved needle is deployed and provides a real-time virtual display of the needle trajectory to the target (curved line) as it is advanced through the needle guide. In the final configuration, real-time imaging with ultrasound or MRI may be used and the needle may be viewed in the scan.

While certain features of the invention have been illustrated and described herein, many modifications, substitutions, changes, and equivalents may occur to those of ordinary skill in the art.

It is, therefore, to be understood that the appended claims are intended to cover all such modifications and changes as fall within the true spirit of the invention.

The invention claimed is:

1. A system for guidance of a curved needle to a target tissue in a body, the system comprising:
    a curved needle having a curved section, the curved section configured to curve in a flexion plane and having a circular arc shape with a constant radius of curvature, said curved needle enclosed within a straight needle guide, such that when enclosed within the straight needle guide, the curved section of the curved needle is straight, and upon distal deployment of the curved needle from the straight needle guide, the curved section that is deployed from the straight needle guide is curved into said circular arc shape with said constant radius of curvature;
    a tracking system having an imaging component, said tracking system configured for tracking a position of said curved needle and a position of said straight needle guide, said imaging component configured for providing a location of the target tissue; and
    a processor configured to algebraically calculate a needle trajectory, the needle trajectory including a needle guide insertion length and a needle deployment length such that said curved needle is configured to reach the target tissue when said needle guide insertion length and said needle deployment length are used, said calculating is done prior to insertion of said needle guide into the body, and wherein said calculating comprises:
    calculating said needle guide insertion length by trigonometric calculations using a distance from and an angle of a chosen entry point with respect to said location of the target tissue; and
    calculating said needle deployment length, wherein said needle deployment length is a length of an arc extending from said needle guide insertion length, said calculating the needle deployment length done based on the constant radius of curvature and an arc center of said curved needle.

2. The system of claim 1, further comprising a tracking sensor positioned on the curved needle, and wherein said tracking system is a tracking system with a three-dimensional tracking capability, and wherein said tracking system is configured to track the position of the curved needle based on data from the tracking sensor.

3. The system of claim 1, wherein said imaging component is configured to provide a scanning plane including the target tissue and an intersection line of the flexion plane with the scanning plane so that a rotated position of the curved needle may be determined for the chosen entry point prior to insertion of the curved needle into the body, such that when in the determined rotated position, the flexion plane of the curved needle includes the target tissue, thus providing the curved needle with capability of reaching the target tissue when deployed from the straight needle guide.

4. The system of claim 1, wherein said imaging component comprises a probe with a two-dimensional scanning plane.

5. The system of claim 4, wherein said curved needle is attached to said probe of said imaging component such that said flexion plane of said curved needle is in alignment with said two-dimensional scanning plane.

6. The system of claim 1, wherein the chosen entry point and an orientation of said entry point determine a vector that is offset from the target tissue.

7. The system of claim 1, wherein the curved needle is a curved injection needle.

8. The system of claim 1, further comprising an automated controller, wherein the processor provides the needle guide insertion length and the needle deployment length based on the constant radius of curvature of the curved needle to the automated controller and the automated controller is configured to advance the needle guide to the needle guide insertion length and the curved needle to the needle deployment length.

9. A method for guidance of a curved needle to a target tissue, the method comprising:
    providing a curved needle having a curved section, the curved section configured to curve in a flexion plane and having a constant curvature radius, said curved needle enclosed within a straight needle guide, such that upon distal deployment of the curved needle from the straight needle guide, the curved section that is deployed from the straight needle guide is curved within the flexion plane in accordance with said constant curvature radius;
    providing a tracking system having an imaging component, said tracking system configured for tracking a position of said curved needle and a position of said straight needle guide, said imaging component configured for providing a location of the target tissue;
    choosing an entry point into a body for said curved needle enclosed within the straight needle guide;
    calculating a needle guide insertion length by trigonometric calculations using a distance from and an angle of the chosen entry point with respect to said location of the target tissue;
    calculating a needle deployment length based on the constant radius of curvature and an arc center of said curved needle, wherein said needle deployment length is a length of an arc extending from said needle guide insertion length; and
    subsequent to said calculating a needle guide insertion length and a needle deployment length, and based on said calculated needle guide insertion length and said needle deployment length:
        positioning the straight needle guide with the curved needle therein at the entry point;
        advancing the straight needle guide with the curved needle therein into the body by said calculated needle guide insertion length; and
        advancing the curved needle distally past a distal end of the straight needle guide by said calculated needle deployment length in order to access the target tissue.

10. The method of claim 9, wherein said positioning the straight needle guide comprises rotating the straight needle guide with the curved needle therein to align a flexion plane of the curved needle such that the target tissue can be accessed upon deployment of the curved needle.

11. The method of claim 9, wherein said positioning the straight needle guide comprises maintaining a position of the straight needle guide and further comprising rotating the curved needle within the straight needle guide to align a flexion plane of the curved needle such that the target tissue can be accessed upon deployment of the curved needle.

12. The method of claim 9, further comprising accessing a second target tissue by calculating a second needle guide insertion length and a second needle deployment length, retracting the curved needle back into the needle guide, repositioning the needle guide at the second needle guide insertion length, and advancing the curved needle distally past a distal end of the straight needle guide by said second needle deployment length.

13. The method of claim 12, wherein said repositioning the needle guide comprises rotating the straight needle guide with the curved needle therein to align a flexion plane of the curved needle such that the target tissue can be accessed upon deployment of the curved needle.

14. The method of claim 12, wherein said repositioning the needle guide comprises maintaining a position of the straight needle guide and further comprising rotating the curved needle within the straight needle guide to align a flexion plane of the curved needle such that the target tissue can be accessed upon deployment of the curved needle.

15. The method of claim 9, further comprising taking a tissue sample once the target tissue is accessed.

16. The method of claim 9, wherein said calculating the needle guide insertion length and the needle deployment length is done by providing a starting orientation vector from a distal end of the straight needle guide to a point which is transversely adjacent the target tissue; providing a target vector from a distal end of the straight needle guide to the target tissue; calculating an angle between the orientation vector and the target vector; and based on the constant curvature radius calculating the projected needle guide insertion length and the needle deployment length.

17. The method of claim 9, further comprising injecting a substance once the target tissue is accessed.

18. The method of claim 9, wherein the chosen entry point and an orientation of said entry point determine a vector that is offset from the target tissue.

* * * * *